(12) United States Patent
Choi et al.

(10) Patent No.: US 7,534,889 B2
(45) Date of Patent: May 19, 2009

(54) 5-HT₄ RECEPTOR AGONIST COMPOUNDS

(75) Inventors: Seok-Ki Choi, Palo Alto, CA (US); Paul Fatheree, San Francisco, CA (US); Adam A Goldblum, San Francisco, CA (US); Lan Jiang, Foster City, CA (US); Daniel D Long, San Francisco, CA (US); Daniel Marquess, Half Moon Bay, CA (US); S. Derek Turner, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 12/136,891

(22) Filed: Jun. 11, 2008

(65) Prior Publication Data

US 2008/0255187 A1 Oct. 16, 2008

Related U.S. Application Data

(62) Division of application No. 11/266,881, filed on Nov. 4, 2005, now Pat. No. 7,399,862.

(60) Provisional application No. 60/625,185, filed on Nov. 5, 2004.

(51) Int. Cl.
*C07D 215/00* (2006.01)
*A01N 43/90* (2006.01)

(52) U.S. Cl. ...................... 546/156; 514/305

(58) Field of Classification Search .................. 546/156
See application file for complete search history.

(56) References Cited

U.S. PATENT DOCUMENTS

| | | | |
|---|---|---|---|
| 4,321,378 A | 3/1982 | Dostert et al. |
| 4,845,092 A | 7/1989 | Sanger et al. |
| 4,853,394 A | 8/1989 | King et al. |
| 4,937,247 A | 6/1990 | King |
| 5,017,573 A | 5/1991 | Kon et al. |
| 5,037,844 A | 8/1991 | Hamminga et al. |
| 5,047,410 A | 9/1991 | Donetti et al. |
| 5,096,901 A | 3/1992 | Ward et al. |
| 5,223,511 A | 6/1993 | Turconi et al. |
| 5,248,684 A | 9/1993 | Suzuki et al. |
| 5,272,154 A | 12/1993 | Dixon et al. |
| 5,298,510 A | 3/1994 | Tyers |
| 5,319,085 A | 6/1994 | Suzuki et al. |
| 5,552,398 A | 9/1996 | King et al. |
| 5,561,149 A | 10/1996 | Azria et al. |
| 5,571,820 A | 11/1996 | Ohuchi et al. |
| 5,654,320 A | 8/1997 | Catlow et al. |
| 5,684,003 A | 11/1997 | Kikuchi et al. |
| 5,696,129 A | 12/1997 | King et al. |
| 5,733,917 A | 3/1998 | Ohuchi et al. |
| 5,741,801 A | 4/1998 | King et al. |
| 5,753,673 A | 5/1998 | Ohuchi et al. |
| 5,773,436 A | 6/1998 | Muller et al. |
| 5,864,039 A | 1/1999 | Kawakita et al. |
| 5,914,405 A | 6/1999 | Wilson |
| 5,945,434 A | 8/1999 | Suzuki et al. |
| 6,002,009 A | 12/1999 | Cereda et al. |
| 6,117,882 A | 9/2000 | Schaus et al. |
| 6,172,062 B1 | 1/2001 | Clark et al. |
| 6,197,769 B1 | 3/2001 | Alisi et al. |
| 6,281,218 B1 | 8/2001 | Cereda et al. |
| 6,294,555 B1 | 9/2001 | Kato et al. |
| 6,452,013 B1 | 9/2002 | Bosmans et al. |
| 6,544,997 B1 | 4/2003 | Bosmans et al. |
| 6,624,162 B2 | 9/2003 | Uchida et al. |
| 6,696,468 B2 | 2/2004 | Kato et al. |
| 6,979,690 B2 | 12/2005 | Gymer et al. |
| 7,317,022 B2 | 1/2008 | Gendron et al. |
| 7,351,704 B2 | 4/2008 | Marquess et al. |
| 7,375,114 B2 | 5/2008 | Marquess et al. |
| 7,396,933 B2 | 7/2008 | Choi et al. |
| 7,399,862 B2 * | 7/2008 | Choi et al. .................. 546/156 |
| 7,419,989 B2 | 9/2008 | Fatheree et al. |
| 2002/0173505 A1 | 11/2002 | Skogvall |
| 2004/0122043 A1 | 6/2004 | Iguchi et al. |
| 2004/0127514 A1 | 7/2004 | Katsu et al. |
| 2004/0266814 A1 | 12/2004 | Noguchi et al. |
| 2005/0277671 A1 | 12/2005 | Ando et al. |
| 2005/0277672 A1 | 12/2005 | Ando et al. |
| 2005/0277673 A1 | 12/2005 | Ando et al. |
| 2006/0229332 A1 | 10/2006 | Fatheree et al. |
| 2007/0270457 A1 | 11/2007 | Marquess et al. |
| 2007/0281970 A1 | 12/2007 | Marquess et al. |
| 2008/0070923 A1 | 3/2008 | Gendron et al. |
| 2008/0167295 A1 | 7/2008 | Choi et al. |
| 2008/0176895 A1 | 7/2008 | Marquess et al. |

FOREIGN PATENT DOCUMENTS

| | | |
|---|---|---|
| EP | 0 309 423 A2 | 3/1989 |
| EP | 0 623 621 A1 | 11/1994 |
| ES | 2 154 605 A1 | 4/2001 |
| IT | 01298271 B1 | 12/1999 |
| JP | 04005289 A2 | 1/1992 |
| JP | 08231544 A2 | 9/1996 |
| WO | WO 93/03725 A1 | 3/1993 |
| WO | WO 97/35860 A1 | 10/1997 |
| WO | WO 99/20633 A1 | 4/1999 |
| WO | WO 00/63215 A2 | 10/2000 |
| WO | WO 01/25236 A2 | 4/2001 |
| WO | WO 02/36113 A1 | 5/2002 |
| WO | WO 2004/026868 A1 | 4/2004 |
| WO | WO 2005/000837 A1 | 1/2005 |

(Continued)

OTHER PUBLICATIONS

EP 05824243.9 Ofc Action, Theravance, Inc.

(Continued)

*Primary Examiner*—D. Margaret Seaman
*Assistant Examiner*—Nizal S Chandrakumar
(74) *Attorney, Agent, or Firm*—Jeffrey A. Hagenah; Roberta P. Saxon

(57) ABSTRACT

The invention provides novel quinolinone-carboxamide 5-HT₄ receptor agonist compounds. The invention also provides pharmaceutical compositions comprising such compounds, methods of using such compounds to treat diseases associated with 5-HT₄ receptor activity, and processes and intermediates useful for preparing such compounds.

16 Claims, No Drawings

FOREIGN PATENT DOCUMENTS

| WO | WO 2005/000838 A1 | 1/2005 |
|---|---|---|
| WO | WO 2005/021539 A1 | 3/2005 |
| WO | WO 2005/049608 | 6/2005 |
| WO | WO 2005/073222 A1 | 8/2005 |
| WO | WO 2005/092882 A1 | 10/2005 |

OTHER PUBLICATIONS

Allegretti et al., "One-pot, new stereoselective synthesis of endo-tropanamine", Tetrahedron Letters 42, pp. 4257-4259 (2001).
Baxter et al., "Benzimidazolone derivatives act as 5-$HT_4$ receptor ligands in rat oesophagus", European Journal of Pharmacology, 212, pp. 225-229 (1992).
Berdini et al., "A modified palladium catalysed reductive amination procedure", Tetrahedron 58, pp. 5669-5674 (2002).
Bermudez et al., "5-Hydroxytryptamine (5-$HT_3$) Receptor Antagonists. 1. Indazole and Indolizine-3-carboxylic Acid Derivatives", J. Med. Chem., 33, pp. 1924-1929 (1990).
Blum et al., "Design and Synthesis of Novel Ligands for the 5-$HT_3$ and the 5-$HT_4$ Receptor", Bioorganic & Medicinal Chemistry Letters, vol. 2, No. 5, pp. 461-466 (1992).
Curtet et al., "New Arylpiperazine Derivatives as Antagonists of the Human Cloned 5-$HT_4$ Receptor Isoforms", J. Med. Chem., 43, pp. 3761-3769 (2000).
Dumuis et al., "Characterization of a novel 5-$HT_4$ receptor antagonist of the azabicycloalkyl benzimidazolone class: DAU 6285", Naunyn-Schmiedeberg's Arch Pharmacol, 345, pp. 264-269 (1992).
Dumuis et al., "Azabicycloalkyl benzimidazolone derivatives as a novel class of potent agonists at the 5-$HT_4$ receptor positively coupled to adenylate cyclase in brain", Naunyn-Schmiedeberg's Arch Pharmacol, 343, pp. 245-251 (1991).
Fake et al., "BRL 43694: A Potent and Novel 5-$HT_3$ Receptor Antagonist", Br. J. Pharmacol., 91, 335P (1987).
Kaumann et al., "Indazole as an Indole Bioisostere:5-$HT_4$ Receptor Antagonism.", Bioorganic & Medicinal Chemistry Letters, vol. 2, No. 5, pp. 419-420 (1992).
Langlois et al., "5-$HT_4$ Receptor Ligands: Applications and New Prospects", J Med Chem, vol. 46, No. 3, pp. 319-344 (2003).
Lopez-Rodriguez et al., "3-D-QSAR/CoMFA and Recognition Models of Benzimidazole Derivatives at the 5-$HT_4$ Receptor", Bioorganic & Medicinal Chemistry Letters, 11, pp. 2807-2811 (2001).
Lopez-Rodriguez et al., "Benzimidazole Derivates. Part 1: Synthesis and Structure-Activity Relationships of New Benzimidazole-4-carboxamides and Carboxylates as Potent and Selective 5-$HT_4$ Receptor Antagonists", Bioorganic & Medicinal Chemistry, 7, pp. 2271-2281 (1999).
Lopez-Rodriguez et al., "Benzimidazole Derivatives. 3. 3D-QSAR/CoMFA Model and Computational Simulation for the Recognition of 5-$HT_4$ Receptor Antagonists", J. Med. Chem., 45, pp. 4806-4815 (2002).
Lopez-Rodriguez et al., "Benzimidazone derivatives 4. The recognition of the voluminous substituent attached to the basic amino group of 5-$HT_4$ receptor antagonists", Journal of Computer-Aided Molecular Design, 17, pp. 515-524 (2003).
Lopez-Rodriguez et al., "Design and Synthesis of New Benzimidazole-Arylpiperazine Derivatives Acting as Mixed 5-$HT_{1A}$/5-$HT_3$ Ligands", Bioorganic & Medicinal Chemistry Letters, 13, pp. 3177-3180 (2003).
Lopez-Rodriguez et al., "Study of the bioactive conformation of novel 5-$HT_4$ receptor ligands: influence of an intramolecular hydrogen bond", Tetrahedron, 57, pp. 6745-6749 (2001).
Schaus et al., "Synthesis and Structure-Activity Relationships of Potent and Orally Active 5-$HT_4$ Receptor Antagonists: Indazole and Benzimidazolone Derivatives", J. Med. Chem., 41, pp. 1943-1955 (1998).
Suzuki et al., "Synthesis and Evaluation of Novel 2-Oxo-1,2-dihydro-3-quinolinecarboxamide Derivatives as Potent and Selective Serotonin 5-$HT_4$ Receptor Agonists", Chem. Pharm. Bull., 49(1), pp. 29-39 (2001).
Suzuki et al., "A Practical Procedure for Preparation of N-(endo-8-3-hydroxy)propyl-8-azabicyclo[3.2.1]oct-3-yl)-1-isopropyl-2-oxo-1,2-dihydro-3-quinoline-carboxamide (TS-951)", Heterocycles, vol. 53, No. 11, pp. 2471-2485 (2000).
Sukuki et al., "Synthesis and Evaluation of Novel 2-Oxo-1,2-dihydro-3-quinolinecarboxamide Derivatives as Serotonin 5-$HT_4$ Receptor Agonists", Chem. Pharm. Bull., 48(12), pp. 2003-2008 (2000).
Tapia et al., "2,3-Dihydro-2-oxo-1H-benzimidazole-1-carboxamides with Selective Affinity for the 5-$HT_4$ Receptor: Synthesis and Structure-Affinity and Structure-Activity Relationships of a New Series of Partial Agonist and Antagonist Derivatives", J. Med. Chem., 42, pp. 2870-2880 (1999).
Turconi et al., "Azabicycloalkyl benzimidazolones: Interaction with serotonergic 5-$HT_3$ and 5-$HT_4$ receptors and potential therapeutic implications", Drugs of the Future, 16(11), pp. 1011-1026 (1991).
Turconi et al., "Synthesis of a New Class of 2,3-Dihydro-2-oxo-1H-benzimidazole-1-carobxylic Acid Derivatives as Highly Potent 5-$HT_3$ Receptor Antagonists", J. Med. Chem., 33, pp. 2101-2108 (1990).
Abstract of JP 04089489 A2, "Preparation of azabicyclo compound quaternary ammonium salts as 5-HT3 receptor antagonists", published Mar. 23, 1992, Chemical Abstracts Accession No. CAN 117:19164.
Abstract of JP 07324087 A2, "Preparation of 2-oxo-1,2-dihydro-4-quinolinecarboxylic acid derivatives as serotonin receptor stimulants", published Dec. 12, 1995, Chemical Abstracts Accession No. CAN 124:260866.
Abstract of JP 08034783 A2, "Preparation of N-(8-azabicyclo[3.2.1]oct-3-yl)-2-oxo,1,2-dihydro-3-quinolinecarboxamide and (8-azabicyclo[3.2.1]oct-3-yl)-2-oxo,1,2-dihydro-3-quinolinecarboxylate derivatives as stimulants of serotonin (5-HT4) receptor", published Feb. 6, 1996, Chemical Abstracts Accession No. CAN 124:343137.
Abstract of JP 08034785 A2, "Preparation of N-(8-azoniabicyclo[3.2.1]oct-3-yl)-2-oxo,1,2-dihydro-3-quinolinecarboxamide and (8-azoniabicyclo[3.2.1]oct-3-yl)-2-oxo,1,2-dihydro-3-quinolinecarboxylate derivatives as stimulants of serotonin 4 (5-HT4) receptor", published Feb. 6, 1996, Chemical Abstracts Accession No. CAN 124:343138.
Abstract of JP 09194374 A2, "Digestive tract disease-treating agents", published Jul. 29, 1997, Chemical Abstracts No. CAN 127:210377.
Abstract of JP 09241241 A2, "Preparation of N-(1-substituted-4-piperidyl)benzamides having serotonin receptor agonist activity", published Sep. 16, 1997, Chemical Abstracts Accession No. CAN 127:293254.
Abstract of JP 11001472 A2, "Preparation of 4-amino-5-halo-2-alkoxy-N-(4-piperidinylalkyl or 4-piperidinyl carbonyl)benzamides for improving digestive tract function", published Jan. 6, 1999, Chemical Abstracts Accession No. CAN 130:139257.
Abstract of JP 2001122784 A2, "Pharmaceuticals containing 1-[(1-substituted 4-piperidinyl)methyl]-4-piperidines as serotonin 4 receptor agonists", published May 8, 2001, Chemical Abstracts Accession No. CAN 134:348274.
Abstract of JP 2004277318 A2, "1-(1-Substitued-4-piperidinylmethyl)piperidine derivatives as 5-HT4 receptor agonists, pharmaceutical compositions containing them, and their use", published Oct. 7, 2004, Chemical Abstracts Accession No. CAN 141:307555.
Abstract of JP 2004277319 A2, "1-(4-piperidinylmethyl)piperidinylamide derivatives as 5-HT4 receptor agonists, pharmaceutical compositions containing them, and their use", published Oct. 7, 2004, Chemical Abstracts Accession No. CAN 141:307556.
Abstract of JP 2004277320 A2, "1,4-disubstituted piperidine derivatives as 5-HT4 receptor agonists, pharmaceutical compositions containing them, and their use", published Oct. 7, 2004, Chemical Abstracts Accession No. CAN 141:307557.
Harada et al., "Novel N-[1-(1-Substituted 4-Piperidinylmethyl)-4-piperidinyl]benzamides as Potent Colonic Prokinetic Agents", BioOrganic & Medicinal Chemistry Letters 12, pp. 967-970 (2002).

* cited by examiner

5-HT₄ RECEPTOR AGONIST COMPOUNDS

CROSS-REFERENCE TO RELATED APPLICATIONS

This application is a divisional application of U.S. application Ser. No. 11/266,881, filed Nov. 4, 2005, now U.S. Pat. No. 7,399,862 which application claims the benefit of U.S. Provisional Application No. 60/625,185, filed on Nov. 5, 2004, the entire disclosures of which are incorporated herein by reference in their entirety.

BACKGROUND OF THE INVENTION

1. Field of the Invention

The invention is directed to quinolinone-carboxamide compounds which are useful as 5-HT₄ receptor agonists. The invention is also directed to pharmaceutical compositions comprising such compounds, methods of using such compounds for treating medical conditions mediated by 5-HT₄ receptor activity, and processes and intermediates useful for preparing such compounds.

2. State of the Art

Serotonin (5-hydroxytryptamine, 5-HT) is a neurotransmitter that is widely distributed throughout the body, both in the central nervous system and in peripheral systems. At least seven subtypes of serotonin receptors have been identified and the interaction of serotonin with these different receptors is linked to a wide variety of physiological functions. There has been, therefore, substantial interest in developing therapeutic agents that target specific 5-HT receptor subtypes.

In particular, characterization of 5-HT₄ receptors and identification of pharmaceutical agents that interact with them has been the focus of significant recent activity. (See, for example, the review by Langlois and Fischmeister, *J. Med. Chem.* 2003, 46, 319-344.) 5-HT₄ receptor agonists are useful for the treatment of disorders of reduced motility of the gastrointestinal tract. Such disorders include irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some 5-HT₄ receptor agonist compounds may be used in the treatment of central nervous system disorders including cognitive disorders, behavioral disorders, mood disorders, and disorders of control of autonomic function.

Despite the broad utility of pharmaceutical agents modulating 5-HT₄ receptor activity, few 5-HT₄ receptor agonist compounds are in clinical use at present.

Accordingly, there is a need for new 5-HT₄ receptor agonists that achieve their desired effects with minimal side effects. Preferred agents may possess, among other properties, improved selectivity, potency, pharmacokinetic properties, and/or duration of action.

SUMMARY OF THE INVENTION

The invention provides novel compounds that possess 5-HT₄ receptor agonist activity. Among other properties, compounds of the invention have been found to be potent and selective 5-HT₄ receptor agonists.

Accordingly, the invention provides a compound of formula (I):

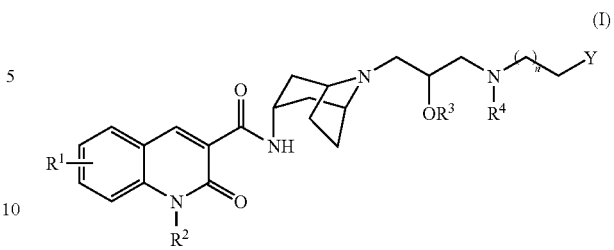

or a pharmaceutically-acceptable salt or solvate or stereoisomer thereof, wherein:

$R^1$ is hydrogen, halo, hydroxy, $C_{1-4}$alkyl, or $C_{1-4}$alkoxy;

$R^2$ is $C_{3-4}$alkyl or $C_{3-6}$cycloalkyl;

$R^3$ is hydrogen or $C_{1-3}$alkyl;

$R^4$ is —S(O)₂—$C_{1-3}$alkyl, —C(O)O—$C_{1-3}$alkyl or —C(O)—$C_{1-3}$alkyl;

n is an integer of 0, 1, 2, or 3;

Y is selected from:

(a) a moiety of formula (a)

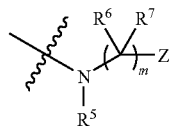

wherein:

Z is selected from —N(R⁸)SO₂Rᵃ, —N(R⁸)C(O)Rᶜ, —S(O₂)R⁸, —N(R⁸)C(O)ORᵈ, —N(R⁸)C(O)NRᵉRᶠ, —N(R⁸)SO₂NRᵍRʰ, —C(O)NRⁱRʲ, —OC(O)NRᵏRˡ, —C(O)ORᵐ, —OR⁸, —SRⁿ, cyano, hydroxy-substituted $C_{1-4}$alkyl, hydroxy-substituted $C_{1-3}$alkoxy, —CF₃, pyridinyl, thiomorpholinyl, thiazolidinyl, imidazolyl, indolyl, tetrahydrofuranyl, pyrrolidinyl and piperidinyl, wherein pyrrolinyl is optionally substituted with oxo and piperidinyl is optionally substituted with 1 to 3 halo;

$R^5$ is selected from hydrogen and $C_{1-4}$alkyl, wherein $C_{1-4}$alkyl is optionally substituted with 1 to 2 substituents selected from hydroxy, halo, and $C_{1-3}$alkoxy;

m is an integer of 0, 1, 2, 3, 4, or 5;

$R^6$ and $R^7$ are independently selected from hydrogen, hydroxy, halo and $C_{1-4}$alkyl, wherein $C_{1-4}$alkyl is optionally substituted with 1 to 2 substituents selected from hydroxy, $C_{1-3}$alkoxy, and cyano;

$R^8$ is independently hydrogen or $C_{1-4}$alkyl, wherein $C_{1-4}$alkyl is optionally substituted with 1 to 2 substituents selected from hydroxy, $C_{1-3}$alkoxy, and cyano;

$R^a$ is hydrogen or $C_{1-4}$alkyl, wherein $C_{1-4}$alkyl is optionally substituted with —SO₂Rᵇ, $C_{3-6}$cycloalkyl or with from 1 to 3 halo;

$R^c$ is hydrogen or $C_{1-4}$alkyl, wherein $C_{1-4}$alkyl is optionally substituted with 1 to 2 substituents selected from hydroxy and $C_{3-6}$cycloalkyl, or with from 1 to 3 halo;

and $R^b$, $R^d$, $R^e$, $R^f$, $R^g$, $R^h$, $R^i$, $R^j$, $R^k$, $R^l$, $R^m$, and $R^n$, are independently hydrogen or $C_{1-4}$alkyl;

or $R^5$ and $R^6$, $R^5$ and $R^8$, or $R^6$ and $R^8$, taken together form a $C_{2-5}$alkylene, wherein the $C_{2-5}$alkylene is optionally substituted with 1 to 2 substituents selected from hydroxy, halo and $C_{1-4}$alkyl, wherein $C_{1-4}$alkyl is optionally substituted with 1 to 2 substituents selected from hydroxy, $C_{1-3}$alkoxy, and cyano;

or $R^8$ and $R^a$ taken together form a $C_{2-5}$alkylene;

provided that when m is 1, Z forms a carbon-carbon bond with the carbon atom bearing the substituents $R^6$ and $R^7$; and when m is 0, Z is selected from —S(O$_2$)R$^8$, —C(O)NR$^i$R$^j$, —C(O)OR$^m$, and —CF$_3$;

(b) —OR$^9$, wherein $R^9$ is hydrogen or $C_{1-4}$alkyl, wherein $C_{1-4}$alkyl is optionally substituted with 1 to 2 substituents selected from hydroxy, $C_{1-3}$alkoxy, and cyano;

(c) —SR$^{10}$, wherein $R^{10}$ is hydrogen or $C_{1-4}$alkyl; and (d) a heterocycle or heteroaryl selected from pyridinyl, thiomorpholinyl, thiazolidinyl, imidazolyl, indolyl, tetrahydrofuranyl, pyrrolidinyl and piperidinyl, wherein pyrrolinyl is optionally substituted with oxo and piperidinyl is optionally substituted with 1 to 3 halo;

provided that when n is 0, Y is selected from (d), wherein the heterocycle or heteroaryl is attached via a carbon atom of the heterocycle or heteroaryl ring.

The invention also provides a pharmaceutical composition comprising a compound of the invention and a pharmaceutically-acceptable carrier.

The invention also provides a method of treating a disease or condition associated with 5-HT$_4$ receptor activity, e.g. a disorder of reduced motility of the gastrointestinal tract, the method comprising administering to the mammal, a therapeutically effective amount of a compound of the invention.

Further, the invention provides a method of treating a disease or condition associated with 5-HT$_4$ receptor activity in a mammal, the method comprising administering to the mammal, a therapeutically effective amount of a pharmaceutical composition of the invention.

The invention provides a method of treating irritable bowel syndrome, the method comprising administering to the mammal, a therapeutically effective amount of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate or stereoisomer thereof, as a research tool for studying a biological system or sample or for discovering new 5-HT$_4$ receptor agonists, the method comprising contacting a biological system or sample with a compound of the invention and determining the effects caused by the compound on the biological system or sample.

In separate and distinct aspects, the invention also provides synthetic processes and novel intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with 5-HT$_4$ receptor activity, e.g. a disorder of reduced motility of the gastrointestinal tract, in a mammal.

DETAILED DESCRIPTION OF THE INVENTION

The invention provides novel quinolinone-carboxamide 5-HT$_4$ receptor agonists of formula (I), or pharmaceutically-acceptable salts or solvates or stereoisomers thereof. The following exemplary and preferred values for radicals, substituents, and ranges, are for illustration only; they do not exclude other defined values or other values within defined ranges for the radicals and substituents unless otherwise indicated.

In a specific aspect of the invention, $R^1$ is hydrogen, halo, $C_{1-4}$alkyl, or $C_{1-4}$alkoxy.

In other specific aspects, $R^1$ is hydrogen, halo, or $C_{1-3}$alkyl; or $R^1$ is fluoro; or $R^1$ is bromo.

In another specific aspect, $R^1$ is hydrogen.

In a specific aspect, $R^2$ is $C_{3-4}$alkyl. Representative $R^2$ groups include n-propyl, isopropyl, n-butyl, sec-butyl, and tert-butyl.

In another specific aspect, $R^2$ is isopropyl.

In yet another specific aspect, $R^2$ is cyclobutyl or cyclopentyl.

In a specific aspect, $R^3$ is hydrogen.

In another specific aspect, $R^3$ is methyl.

In a specific aspect, $R^4$ is —S(O)$_2$—C$_{1-3}$alkyl. In another specific aspect, $R^4$ is —S(O)$_2$CH$_3$.

In yet another specific aspect, $R^4$ is —C(O)O—C$_{1-3}$alkyl. Representative $R^4$ groups include —C(O)OCH$_3$, —C(O)OCH$_2$CH$_3$, —C(O)OCH(CH$_3$)$_2$, and —C(O)OCH$_2$CH$_2$CH$_3$.

In another specific aspect, $R^4$ is —C(O)OCH$_3$.

In yet another specific aspect, $R^4$ is —C(O)—C$_{1-3}$alkyl. Representative $R^4$ groups include —C(O)CH$_3$, —C(O)CH$_2$CH$_3$, —C(O)CH(CH$_3$)$_2$, and —C(O)CH$_2$CH$_2$CH$_3$.

In another specific aspect, $R^4$ is —C(O)CH$_3$.

In yet another specific aspect, $R^4$ is selected from —S(O)$_2$CH$_3$, —C(O)OCH$_3$, and —C(O)CH$_3$.

In a specific aspect, n is an integer of 0, 1, or 2. In another specific aspect, n is an integer of 1, 2, or 3. In other specific aspects, n is 1 or 2; or n is 1.

In a specific aspect, Y is selected from:

(a) a moiety of formula (a), wherein Z is selected from —N(R$^8$)SO$_2$R$^a$, —N(R$^8$)C(O)R$^c$, —S(O$_2$)R$^8$, —N(R$^8$)C(O)NR$^e$R$^f$, —C(O)NR$^i$R$^j$, —OC(O)NR$^k$R$^l$, —OR$^8$, and cyano;

(b) —O—C$_{1-4}$alkyl, wherein C$_{1-4}$alkyl is optionally substituted with 1 to 2 substituents selected from hydroxy;

(c) —S—C$_{1-4}$alkyl; and (d) pyridinyl, imidazolyl, indolyl, and tetrahydrofuranyl, wherein pyrrolidinyl is optionally substituted with oxo.

In another specific aspect of the invention, Y is a moiety of formula (a).

In another specific aspect of the invention, Y is —OR$^9$.

In yet another specific aspect, Y is —O—C$_{1-3}$alkyl, wherein C$_{1-3}$alkyl is optionally substituted with 1 to 2 substituents selected from hydroxy, C$_{1-3}$alkoxy, and cyano. In other specific aspects of the invention, Y is —SR$^{10}$; or Y is —S—C$_{1-3}$alkyl.

In yet another aspect of the invention, Y is a heterocycle or heteroaryl selected from pyridinyl, thiomorpholinyl, thiazolidinyl, imidazolyl, indolyl, tetrahydrofuranyl, pyrrolidinyl and piperidinyl, wherein pyrrolinyl is optionally substituted with oxo and piperidinyl is optionally substituted with 1 to 3 halo. In another specific aspect, Y is selected from pyridinyl, imidazolyl, indolyl, and tetrahydrofuranyl, wherein pyrrolidinyl is optionally substituted with oxo.

In specific aspects, Z is selected from —N(R$^8$)SO$_2$R$^a$, —N(R$^8$)C(O)R$^c$, —S(O$_2$)R$^8$, —N(R$^8$)C(O)OR$^d$, —N(R$^8$)C(O)NR$^e$R$^f$, —N(R$^8$)SO$_2$NR$^g$R$^h$, —C(O)NR$^i$R$^j$, —OC(O)NR$^k$R$^l$, —C(O)OR$^m$, —OR$^8$, —SR$^n$, and cyano; or Z is selected from —N(R$^8$)SO$_2$R$^a$, —N(R$^8$)C(O)R$^c$, —S(O$_2$)R$^8$, —N(R$^8$)C(O)NR$^e$R$^f$, —C(O)NR$^i$R$^j$, —OC(O)NR$^k$R$^l$, —OR$^8$, and cyano.

In another specific aspect, Z is selected from —N(R$^8$)SO$_2$R$^a$, —N(R$^8$)C(O)R$^c$, —S(O$_2$)R$^8$, and —N(R$^8$)C(O)NR$^e$R$^f$.

In still another specific aspect, Z is —N(R$^8$)SO$_2$R$^a$.

In a specific aspect, R$^5$ is C$_{1-4}$alkyl wherein C$_{1-4}$ alkyl is optionally substituted with 1 to 2 substituents selected from hydroxy, halo, and C$_{1-3}$alkoxy. In one aspect, R$^5$ is methyl. In another specific aspect, R$^5$ is hydrogen.

In a specific aspect, m is an integer of 0, 1, 2, 3 or 4. In another specific aspect, m is an integer of 1, 2, 3 or 4. In other specific aspects, m is 0, 1, 2 or 3; m is 1, 2 or 3; m is 2, 3 or 4; m is 2 or 3; or m is 2.

In a specific aspect, R$^6$ and R$^7$ are independently selected from hydrogen and C$_{1-4}$alkyl, wherein C$_{1-4}$alkyl is optionally substituted with 1 to 2 substituents selected from hydroxy, C$_{1-3}$alkoxy, and cyano. In other specific aspects, R$^6$ and R$^7$ are independently hydrogen and methyl; or R$^6$ and R$^7$ are hydrogen.

In a specific aspect, R$^8$ is selected from hydrogen and C$_{1-4}$alkyl, such as hydrogen and methyl.

In a specific aspect, R$^a$ and R$^c$ are independently selected from hydrogen and C$_{1-4}$alkyl.

In a specific aspect, R$^b$, R$^d$, R$^e$, R$^f$, R$^g$, R$^h$, R$^i$, R$^j$, R$^k$, R$^l$, R$^m$, and R$^n$ are independently selected from hydrogen and methyl.

In another specific aspect of the invention, R$^5$ and R$^6$, or R$^5$ and R$^8$ taken together form an optionally substituted C$_{2-5}$alkylene.

In another specific aspect, R$^5$ and R$^6$, or R$^5$ and R$^8$ taken together form ethylene, or propylene.

In a specific aspect, R$^6$ and R$^8$ taken together form an optionally substituted C$_{2-5}$alkylene.

In another specific aspect, R$^6$ and R$^8$ taken together form ethylene, or propylene.

In a specific aspect, R$^8$ and R$^a$ taken together form a C$_{2-5}$alkylene.

In a specific aspect, R$^9$ is an optionally substituted C$_{1-3}$alkyl.

In a specific aspect, R$^{10}$ is C$_{1-3}$alkyl.

In a specific aspect, the invention provides a compound of formula (I) wherein R$^1$ is hydrogen, R$^2$ is C$_{3-4}$alkyl, and R$^3$ is hydrogen.

In another specific aspect, the invention provides a compound of formula (I) wherein R$^1$ is hydrogen or halo; R$^2$ is isopropyl or C$_{4-5}$cycloalkyl; R$^3$ is hydrogen or methyl, and R$^4$, n and Y are as defined herein.

In another specific aspect, the invention provides a compound of formula (I) wherein n is 1, and when Y is a moiety of formula (a), m is 1, 2 or 3.

In yet another specific aspect, the invention provides a compound of formula (I) wherein:

R$^1$ is hydrogen;
R$^2$ is C$_{3-4}$alkyl;
R$^3$ is hydrogen;
Y is selected from:
(a) a moiety of formula (a):

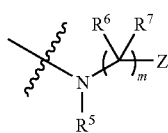

(a)

wherein Z is selected from —N(R$^8$)SO$_2$R$^a$, —N(R$^8$)C(O)R$^c$, —S(O$_2$)R$^8$, —N(R$^8$)C(O)NR$^e$R$^f$, —C(O)NR$^i$R$^j$, —OC(O)NR$^k$R$^l$, —OR$^8$, and cyano;

(b) —O—C$_{1-4}$alkyl, wherein C$_{1-4}$alkyl is optionally substituted with 1 to 2 substituents selected from hydroxy;

(c) —S—C$_{1-4}$alkyl; and (d) pyridinyl, imidazolyl, indolyl, and tetrahydrofuranyl, wherein pyrrolidinyl is optionally substituted with oxo;

and R$^4$, n, m, R$^5$, R$^6$, R$^7$, R$^8$, R$^a$, R$^c$, R$^e$, R$^f$, R$^i$, R$^j$, R$^k$, and R$^l$ are as defined herein.

In yet another specific aspect, the invention further provides a compound of formula (I) which is a compound of formula (II):

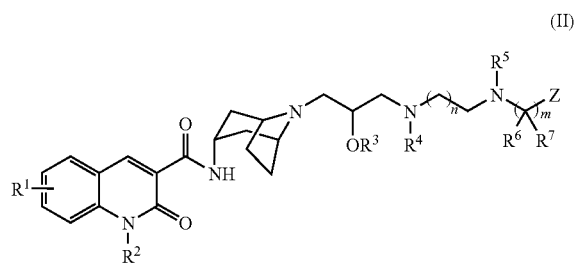

(II)

wherein

R$^1$ is hydrogen, halo, or C$_{1-3}$alkyl;

R$^2$ is C$_{3-4}$alkyl;

R$^3$ is hydrogen or methyl,

R$^4$ is —S(O)$_2$—C$_{1-3}$alkyl, —C(O)O—C$_{1-3}$alkyl, or —C(O)—C$_{1-3}$alkyl;

n is an integer of 1 or 2;

R$^5$ is selected from hydrogen and C$_{1-4}$alkyl, wherein C$_{1-4}$ alkyl is optionally substituted with 1 to 2 substituents selected from hydroxy, halo, and C$_{1-3}$alkoxy;

m is an integer of 1, 2, 3, 4, or 5;

R$^6$ and R$^7$ are independently selected from hydrogen and C$_{1-4}$alkyl, wherein C$_{1-4}$alkyl is optionally substituted with 1 to 2 substituents selected from hydroxy, C$_{1-3}$alkoxy, and cyano;

Z is selected from —N(R$^8$)SO$_2$R$^a$, —N(R$^8$)C(O)R$^c$, —S(O$_2$)R$^8$, —N(R$^8$)C(O)OR$^d$, —N(R$^8$)C(O)NR$^e$R$^f$, —N(R$^8$)SO$_2$NR$^g$R$^h$, —C(O)NR$^i$R$^j$, —OC(O)NR$^k$R$^l$, —C(O)OR$^m$, —OR$^8$, —SR$^n$, and cyano;

R$^8$ is independently hydrogen or C$_{1-4}$alkyl, wherein C$_{1-4}$alkyl is optionally substituted with 1 to 2 substituents selected from hydroxy, C$_{1-3}$alkoxy, and cyano;

R$^a$ is hydrogen or C$_{1-4}$alkyl, wherein C$_{1-4}$alkyl is optionally substituted with —SO$_2$R$^b$, C$_{3-6}$cycloalkyl or with from 1 to 3 halo;

R$^c$ is hydrogen or C$_{1-4}$alkyl, wherein C$_{1-4}$alkyl is optionally substituted with 1 to 2 substituents selected from hydroxy and C$_{3-6}$cycloalkyl, or with from 1 to 3 halo;

and R$^b$, R$^d$, R$^e$, R$^f$, R$^g$, R$^h$, R$^i$, R$^j$, R$^k$, R$^l$, R$^m$, and R$^n$, are independently hydrogen or C$_{1-4}$alkyl;

or R$^5$ and R$^6$, R$^5$ and R$^8$, or R$^6$ and R$^8$, taken together form a C$_{2-5}$alkylene, wherein the C$_{2-5}$alkylene is optionally substituted with 1 to 2 substituents selected from hydroxy, halo and C$_{1-4}$alkyl, wherein C$_{1-4}$alkyl is optionally substituted with 1 to 2 substituents selected from hydroxy, C$_{1-3}$alkoxy, and cyano;

or R$^8$ and R$^a$ taken together form a C$_{2-5}$alkylene.

In still other aspects, the invention provides the compounds listed in Tables 1 to 6 herein, i.e., compounds of formulae (II-a), (II-b), (II-c), (II-d), (II-e), and (II-f).

The chemical naming conventions used herein are illustrated for the compound of Example 2:

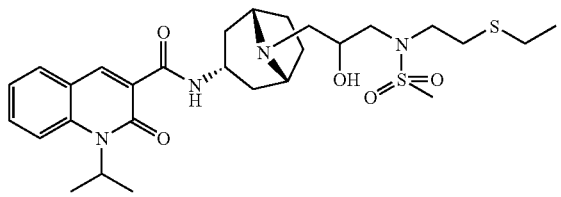

which is designated 1-isopropyl-2-oxo-1,2-dihydroquinoline-3-carboxylic acid ((1S,3R,5R)-8-{3-[(2-ethylsulfanylethyl)methanesulfonylamino]-2-hydroxypropyl}-8-azabicyclo[3.2.1]oct-3-yl)amide, according to the AutoNom software, provided by MDL Information Systems, GmbH (Frankfirt, Germany). The designation (1S,3R,5R) describes the relative orientation of the bonds associated with the bicyclic ring system that are depicted as solid and dashed wedges. The compound is alternatively denoted as N-[(3-endo)-8-{3-[(2-ethylsulfanylethyl)methanesulfonylamino]-2-hydroxypropyl}-8-azabicyclo[3.2.1]oct-3-yl]-1-(1-methylethyl)-2-oxo-1,2-dihydro-3-quinolinecarboxamide. In all of the compounds of the invention listed by name below, the quinolinone carboxamide is endo to the azabicyclooctane group.

Particular mention may be made of the following compounds:

1-isopropyl-2-oxo-1,2-dihydroquinoline-3-carboxylic acid ((1S,3R,5R)-8-{2-hydroxy-3-[(3-imidazol-1-yl-propyl)methanesulfonylamino]propyl}-8-azabicyclo[3.2.1]oct-3-yl)amide;

1-isopropyl-2-oxo-1,2-dihydroquinoline-3-carboxylic acid ((1S,3R,5R)-8-{3-[(2-ethylsulfanylethyl)methanesulfonylamino]-2-hydroxypropyl}-8-aza-bicyclo[3.2.1]oct-3-yl)amide;

1-isopropyl-2-oxo-1,2-dihydroquinoline-3-carboxylic acid ((1S,3R,5R)-8-{3-[(2-ethylsulfanylethyl)methanesulfonylamino]-2-hydroxy-propyl}-8-azabicyclo[3.2.1]oct-3-yl)amide;

(2-hydroxy-3-{(1S,3R,5R)-3-[(1-isopropyl-2-oxo-1,2-dihydro-quinoline-3-carbonyl)amino]-8-azabicyclo[3.2.1]oct-8-yl}propyl)-{2-[3-(methanesulfonylmethylamino)piperidin-1-yl]ethyl}-carbamic acid methyl ester;

[2-(3-acetylaminopiperidin-1-yl)ethyl]-(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-carbamic acid methyl ester;

[2-(3-acetylaminopyrrolidin-1-yl)ethyl]-(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-carbamic acid methyl ester;

(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-[2-(3-dimethylaminosulfonyl-aminopyrrolidin-1-yl)-ethyl]-carbamic acid methyl ester;

(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-[2-(3-dimethylaminosulfonyl methylaminopyrrolidin-1-yl)-ethyl]-carbamic acid methyl ester;

{2-[3-(1,1-dioxo-1$\lambda^6$-isothiazolidin-2-yl)pyrrolidin-1-yl]ethyl}-(2-hydroxy-3-{(1S,3R,5R)-3-[(1-isopropyl-2-oxo-1,2-dihydroquinoline-3-carbonyl)amino]-8-aza-bicyclo[3.2.1]oct-8-yl}propyl)-carbamic acid methyl ester;

1-isopropyl-2-oxo-1,2-dihydroquinoline-3-carboxylic acid [(1S,3R,5R)-8-(3-{acetyl-[2-(3-carbamoylpiperidin-1-yl)ethyl]amino}-2-hydroxypropyl)-8-azabicyclo[3.2.1]oct-3-yl]-amide;

1-isopropyl-2-oxo-1,2-dihydroquinoline-3-carboxylic acid {(1S,3R,5R)-8-[3-(acetyl-{2-[4-(methanesulfonylaminomethyl)piperidin-1-yl]ethyl}amino)-2-hydroxypropyl]-8-aza-bicyclo[3.2.1]oct-3-yl}amide;

(1-{2-[acetyl-(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)amino]-ethyl}pyrrolidin-3-yl)-carbamic acid methyl ester;

1-isopropyl-2-oxo-1,2-dihydroquinoline-3-carboxylic acid {(1S,3R,5R)-8-[3-(acetyl-{2-[3-(dimethylaminosulfonylmethylamino)pyrrolidin-1-yl]ethyl}amino)-2-hydroxypropyl]-8-aza-bicyclo[3.2.1]oct-3-yl}amide;

1-isopropyl-2-oxo-1,2-dihydroquinoline-3-carboxylic acid {(1S,3R,5R)-8-[3-(acetyl-{2-[3-(trimethylureido)pyrrolidin-1-yl]ethyl}amino)-2-hydroxy-propyl]-8-azabicyclo-[3.2.1]oct-3-yl}amide;

1-isopropyl-2-oxo-1,2-dihydroquinoline-3-carboxylic acid {(1S,3R,5R)-8-[3-(acetyl-{2-[(1-dimethylsulfamoylpyrrolidin-3-yl)methylamino]ethyl}amino)-2-hydroxypropyl]-8-azabicyclo[3.2.1]oct-3-yl}amide;

1-isopropyl-2-oxo-1,2-dihydroquinoline-3-carboxylic acid ((1S,3R,5R)-8-{3-[acetyl-(2-{[2-(methanesulfonylmethylamino)ethyl]methylamino}-ethyl)amino]-2-hydroxypropyl}-8-azabicyclo[3.2.1]oct-3-yl)amide;

1-isopropyl-2-oxo-1,2-dihydroquinoline-3-carboxylic acid {(1S,3R,5R)-8-[3-(acetyl-{2-[(2-methanesulfonyl amino ethyl)methylamino]ethyl}amino)-2-hydroxypropyl]-8-aza-bicyclo[3.2.1]oct-3-yl}amide; and 1-isopropyl-2-oxo-1,2-dihydroquinoline-3-carboxylic acid ((1S,3R,5R)-8-{3-[acetyl-(2-{[2-(1,1-dioxo-1$\lambda^6$-isothiazolidin-2-yl)ethyl]methylamino}ethyl)amino]-2-hydroxypropyl}-8-azabicyclo[3.2.1]oct-3-yl)amide.

As exemplified by particular compounds listed above, the compounds of the invention may contain one or more chiral centers. Accordingly, the invention includes racemic mixtures, pure stereoisomers, and stereoisomer-enriched mixtures of such isomers, unless otherwise indicated. When a particular stereoisomer is shown, it will be understood by those skilled in the art, that minor amounts of other stereoisomers may be present in the compositions of the invention unless otherwise indicated, provided that any utility of the composition as a whole is not eliminated by the presence of such other isomers.

DEFINITIONS

When describing the compounds, compositions and methods of the invention, the following terms have the following meanings, unless otherwise indicated.

The term "alkyl" means a monovalent saturated hydrocarbon group which may be linear or branched or combinations thereof. Examples of particular values for a $C_{1-4}$alkyl group include, by way of example, methyl, ethyl, n-propyl (n-Pr), isopropyl (i-Pr), n-butyl (n-Bu), sec-butyl, isobutyl, and tert-butyl.

The term "alkylene" means a divalent saturated hydrocarbon group which may be linear or branched or combinations thereof. Examples of particular values for a $C_{2-5}$alkylene include ethylene, propylene, isopropylene, butylene, and pentylene, and the like.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative $C_{3-6}$cycloalkyl groups include, by way of example, cyclopropyl, cyclobutyl, cyclopentyl, cyclohexyl, and the like.

The term "compound" means a compound that was synthetically prepared or prepared in any other way, such as by metabolism.

The term "halo" means a fluoro, chloro, bromo or iodo.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, benzenesulfonic, benzoic, camphorsulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), napthalene-1,5-disulfonic acid and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

The term "hydroxy protecting group" means a protecting group suitable for preventing undesired reactions of a hydroxyl group. The term "hydroxyl-protecting group" means a protecting group suitable for preventing undesirable reactions at a hydroxyl group. Representative hydroxyl-protecting groups include, but are not limited to, silyl groups including tri(1-6C)alkylsilyl groups, such as trimethylsilyl (TMS), triethylsilyl (TES), tert-butyldimethylsilyl (TBS) and the like; esters (acyl groups) including (1-6C)alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like. Additionally, two hydroxyl groups can also be protected as an alkylidene group, such as prop-2-ylidine, formed, for example, by reaction with a ketone, such as acetone.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

The substituents and variables shown in the following schemes have the definitions provided herein unless otherwise indicated.

In one method of synthesis, compounds of formula (I) are prepared as illustrated in Scheme A:

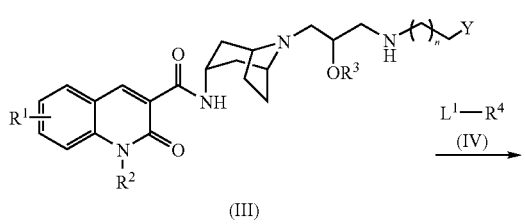

-continued

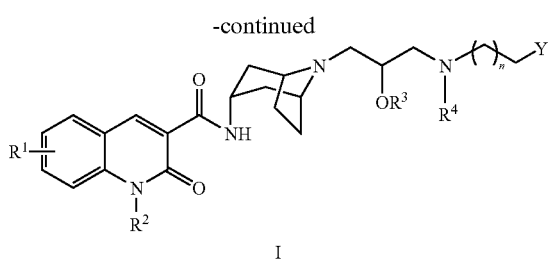

I

In Scheme A, a compound of formula (III) wherein $R^1$, $R^2$, $R^3$, n and Y are as defined herein, is reacted with a compound of formula (IV) wherein $L^1$ is a leaving group, such as halo, for example, chloro, or ethoxy, or $L^1$-$R^4$ is a carboxylic acid, i.e., $L^1$ represents a hydroxy group.

Optimal reaction conditions for the reaction of Scheme A may vary depending on the chemical properties of the reagent $L^1$-$R^4$, as is well known to those skilled in the art.

For example, when $L^1$ is a halo leaving group, such as chloro, the reaction is typically conducted by contacting a compound of formula (III) with between about 1 and about 4 equivalents of a compound of formula (IV) in an inert diluent, such as dichloromethane, in the presence of an excess of a base, for example, between about 3 and about 6 equivalents of base, such as N,N-diisopropylethylamine or 1,8-diazabicyclo [5.4.0]undec-7-ene (DBU). Suitable inert diluents also include N,N-dimethylformamide (DMF), trichloromethane, 1,1,2,2-tetrachloroethane, tetrahydrofuran, and the like. The reaction is typically conducted at a temperature in the range of about −100° C. to about 30° C. for about a quarter hour to about 2 hours, or until the reaction is substantially complete. Exemplary reagents $L^1$-$R^4$ include methanesulfonylchloride and acetylchloride, and the like.

When the reagent $L^1$-$R^4$ is a carboxylic acid, Scheme A represents an amide coupling reaction which is typically conducted by contacting a compound of formula (III) with between about 1 and about 4 equivalents of a carboxylic acid in an inert diluent, for example, N,N-dimethylformamide, in the presence of a coupling agent such as benzotriazol-1-yloxytripyrrolidino-phosphonium hexafluorophosphate (Py-BOP). The reaction is typically conducted at ambient temperature, for about a quarter hour to about 2 hours, or until the reaction is substantially complete. Suitable alternative coupling agents include 1,3 dicyclohexylcarbodiimide (DCC), 1-(3-dimethylaminopropyl)-3-ethylcarbodimide (EDC), and PyBOP combined with 1-hydroxy-7-azabenzotriazole (HOAt).

The amide coupling of a compound of formula (III) with a carboxylic acid alternatively can be performed by converting the carboxylic acid to an activated ester, such as an N-hydroxy succinimide (NHS) ester or a p-nitrophenyl ester, or an acid imidazole, which is then reacted with a compound of formula (III).

When the reagent $L^1$-$R^4$ is a liquid, for example ethyl formate, the reaction can be performed by dissolving a compound of formula (III) in a large excess of the reagent $L^1$-$R^4$, and heating to a temperature of between about 50° C. and about 100° C. for about 12 to about 24 hours.

The product of formula (I) is isolated and purified by conventional procedures. For example, the product can be concentrated to dryness under reduced pressure, taken up in an aqueous weak acid solution and purified by HPLC chromatography.

Similarly, compounds of formula (I) can also be prepared by N-alkylating a compound of the form of formula (I) in which $R^2$ is hydrogen, which can be prepared by the schemes described herein, except substituting the appropriate reagents. The N-alkylation reaction is typically conducted by contacting a compound of the form of formula (I) in which $R^2$ is hydrogen, with between about 1 and about 4 equivalents of a compound of the formula $L^2$-$R^2$ in which $L^2$ is a leaving group such as halo (chloro, iodo or bromo), or a sulfonic ester group, such as mesylate, tosylate, brosylate, nosylate and the like; and $R^2$ is $C_{3\text{-}4}$alkyl or $C_{3\text{-}6}$cycloalkyl. This reaction is typically conducted in a polar aprotic solvent such as dimethylformamide in the presence of between about 2 and about 4 equivalents of strong base, such as potassium tert-butoxide. Typically, the reaction is conducted at a temperature of between about 60° C. and about 100° C. for between about 6 and about 24 hours, or until the reaction is substantially complete.

In yet another alternative, compounds of formula (I) in which $R^1$ is other than hydrogen are prepared by conventional processes from compounds of formula (I) in which $R^1$ is hydrogen.

In another method of synthesis, compounds of formula (II) can be prepared as illustrated in Scheme B:

Scheme B

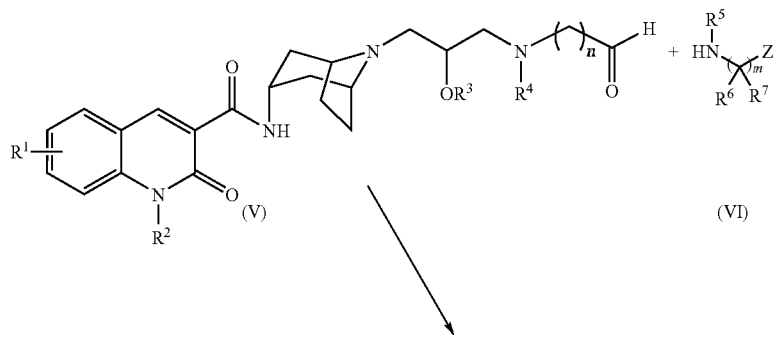

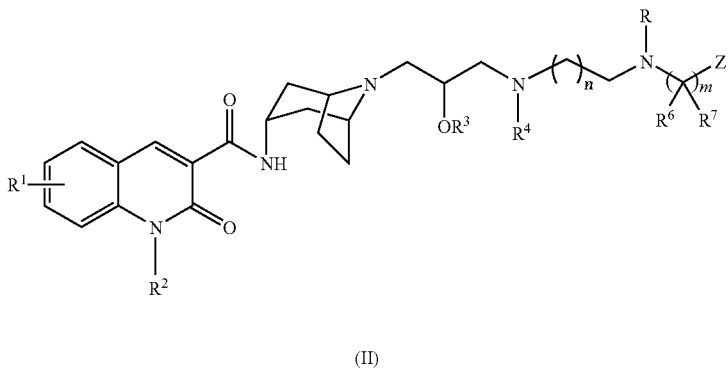

(II)

by reductive amination of an aldehyde of formula (V) or a hydrate of an aldehyde (V). The reductive amination is typically conducted by contacting a compound of formula (V) with between about 1 and about 6 equivalents of an amine compound of formula (VI) in the presence of a reducing agent. Suitable reducing agents, for example, include hydrogen in the presence of a Group VIII metal catalyst, such as palladium on charcoal, or a borohydride, such as sodium triacetoxyborohydride, sodium cyanoborohydride, lithium cyanoborohydride, and the like. Convenient solvents include halogenated hydrocarbons, such as dichloromethane (DCM), and alcohols, such as methanol. Typically, the reaction is conducted at a temperature of between about 0° C. and about 40° C. for between about 0.5 hour and about 4 hours, or until the reaction is substantially complete.

Optimal reaction conditions for the reaction of Scheme B may vary depending on the chemical properties of a compound of formula (VI), as is well known to those skilled in the art. Compounds of formula (VI) are available from commercial sources or can be prepared from readily available starting materials, as discussed in the Examples contained herein.

A compound of formula (III) can be prepared as illustrated in Scheme C:

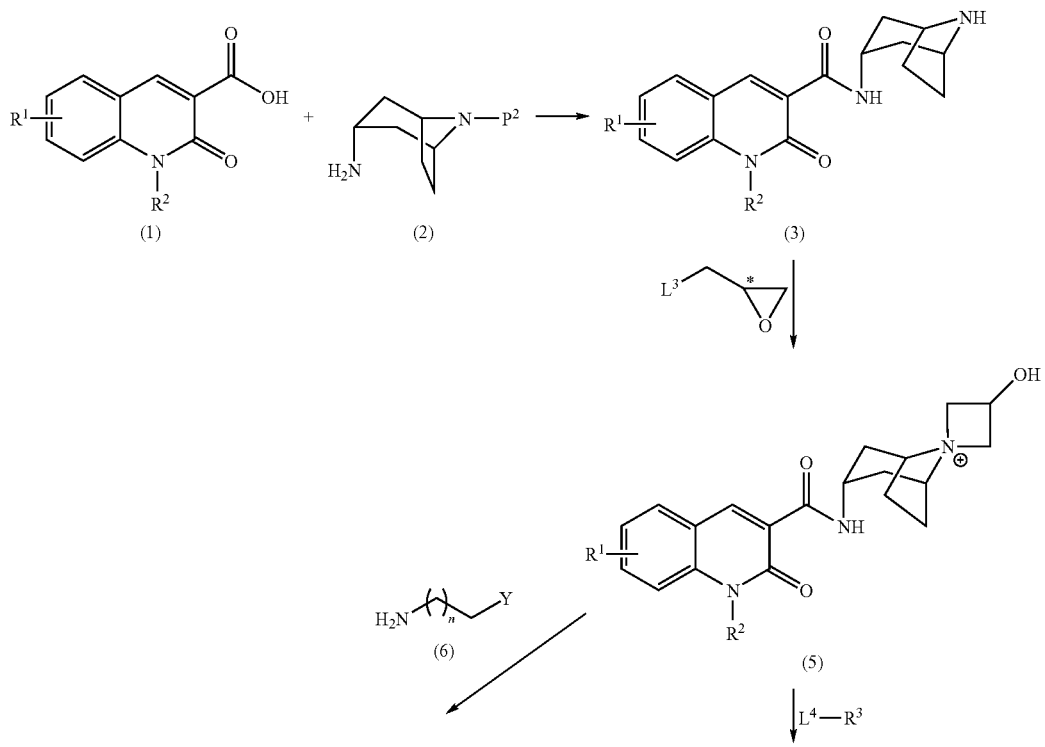

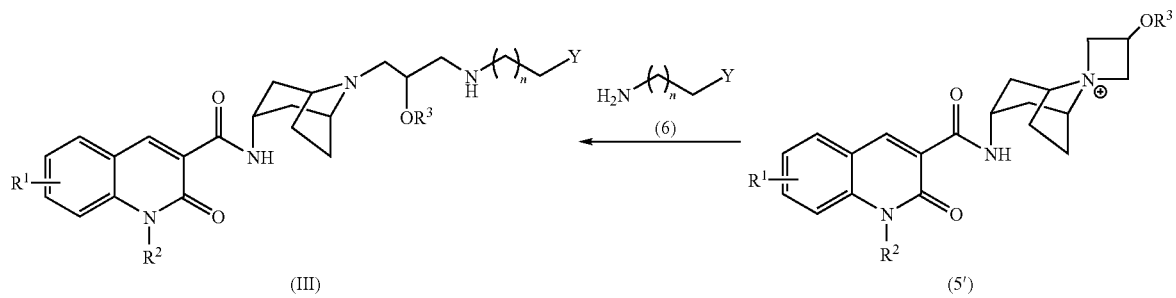

(III)                                                                                 (5')

wherein $P^2$ is an amino-protecting group; and $L^3$ and $L^4$ are leaving groups.

A negatively-charged counterion is also present associated with the positively-charged intermediate compound (5) or (5').

A substituted quinolinone carboxylic acid (1) can be readily prepared by procedures similar to those reported in the literature in Suzuki et al, *Heterocycles*, 2000, 53, 2471-2485 and described in the examples below.

A protected aminotropane (2) or aminoazabicyclooctane can be prepared from readily available starting materials. For example, when the protecting group $P^2$ is Boc, the protected tropane can be prepared by contacting 2,5-dimethoxy tetrahydrofuran with between about 1 and 2 equivalents, preferably about 1.5 equivalents of benzyl amine and a slight excess, for example about 1.1 equivalents, of 1,3-acetonedicarboxylic acid in an acidic aqueous solution in the presence of a buffering agent such as sodium hydrogen phosphate. The reaction mixture is heated to between about 60° C. and about 100° C. to ensure decarboxylation of any carboxylated intermediates in the product, 8-benzyl-8-azabicyclo[3.2.1]octan-3-one, commonly N-benzyltropanone. The product is typically reacted with a slight excess of di-tert-butyl dicarbonate, for example, about 1.1 equivalents, under a hydrogen atmosphere in the presence of a transition metal catalyst to provide a Boc protected intermediate, 3-oxo-8-azabicyclo[3.2.1]octane-8-carboxylic acid tert-butyl ester. The reaction is typically conducted at ambient temperature for about 12 to about 72 hours. Finally, the ester is contacted with a large excess, for example between about 10 to about 40 equivalents, of ammonium formate in an inert diluent, such as methanol, in the presence of a transition metal catalyst to provide an aminotropane in the endo configuration, typically, more than 99% in the endo configuration. The product can be purified by conventional procedures, such as by alkaline extraction.

Intermediate compound (3) can be prepared by coupling a substituted quinolinone carboxylic acid (1) with a protected aminotropane (2) under conditions similar to those described in Scheme A for amide bond formation. The protecting group $P^2$ can be removed by standard procedures to provide an intermediate compound (3). For example when the protecting group is Boc, typically removal is by treatment with an acid, such as trifluoroacetic acid, providing the acid salt of the intermediate. The acid salt of intermediate compound (3) can be converted to the free base, if desired, by conventional treatment with base. The protecting group Cbz, for another example, is conveniently removed by hydrogenolysis over a suitable metal catalyst, such as palladium on carbon.

It will be understood that in the reaction described above, and in other processes described herein using intermediate compound (3), intermediate compound (3) can be supplied in the form of the free base or in a salt form, with appropriate adjustment of reaction conditions, as necessary, as known to those skilled in the art.

An azetidine intermediate (5) can be prepared by reacting intermediate compound (3) with an oxirane compound, wherein $L^3$ represents a leaving group such as bromo, chloro, or iodo, to form an azetidine salt of formula (5). The oxirane compound can be, for example, 2-bromomethyloxirane (commonly, epibromohydrin). This reaction is typically conducted by contacting intermediate compound (3) with between about 2 and about 4 equivalents of 2-bromomethyloxirane in a polar diluent, such as ethanol. The reaction is typically conducted at ambient temperature for between about 24 and about 48 hours or until the reaction is substantially complete.

An azetidine intermediate of formula (5'), in which $R^3$ is $C_{1-3}$alkyl, can be prepared by contacting intermediate (5) with from slightly less than one equivalent to about one equivalent of a compound of formula $L^4$-$R^3$, where $R^3$ is $C_{1-3}$alkyl, and $L^4$ is a leaving group, such as halo (chloro, bromo, or iodo) or the like; in an inert diluent in the presence of between about 1 and about 3 equivalents of a strong base, such as potassium tert-butoxide or sodium hydride. The reaction is typically conducted at ambient temperature for between about a quarter hour to an hour, or until the reaction is substantially complete. Suitable inert diluents include dichloromethane, trichloromethane, 1,1,2,2-tetrachloroethane, and the like.

A compound of formula (III) can be prepared by reacting an azetidine compound of formula (5) or (5') with an amine compound of formula (6) in the presence of a base to provide a compound of formula (III). Typically, the azetidine intermediate is dissolved in an inert diluent, such as methanol, in the presence of a base, and contacted with between about 1 and about 8 equivalents, such as between about 1 and 3 equivalents, of the amine. The reaction is typically conducted at a temperature of between about 0° C. and about 100° C. for between about 12 and about 24 hours or until the reaction is substantially complete.

A compound of formula (V) can be prepared as illustrated in Scheme D:

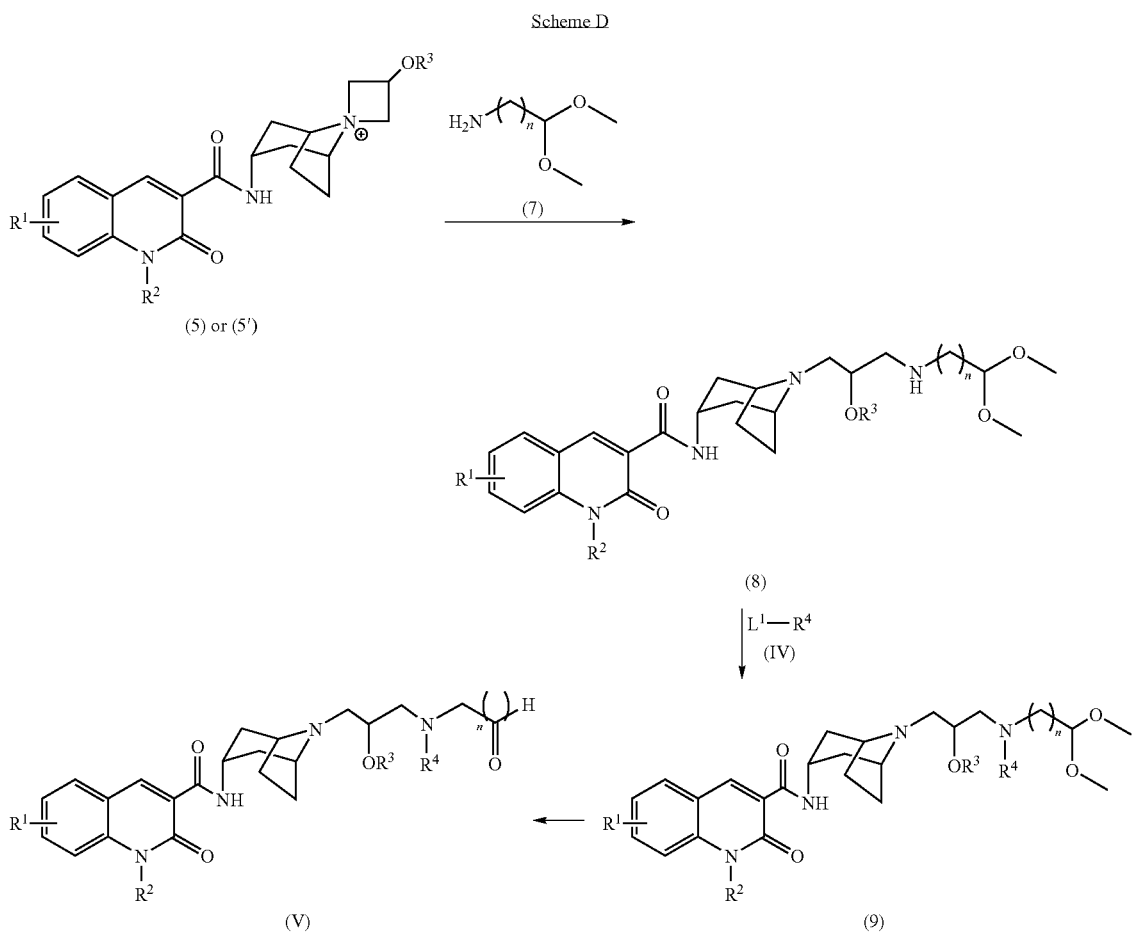

In Scheme D, an azetidine intermediate (5) or (5'), wherein $R^3$ is hydrogen or $C_{1-3}$alkyl respectively, is reacted with an amino acetal (7). The acetal intermediate (8) product is then reacted with a compound of formula (IV), $L^1$-$R^4$, wherein $L^1$ is a leaving group, to provide an aminoacetal intermediate (9). The aminoacetal intermediate (9) is then hydrolyzed to form an aldehyde compound of formula (V) or the hydrate of aldehyde (V). The process of Scheme D is described further in Examples 3-4.

A solution of an azetidine intermediate in an inert diluent, such as ethanol, is mixed with an amino acetal (7), such as aminoacetaldehyde dimethylacetal, in the presence of a base. Suitable bases include DIPEA, DBU and the like. The mixture is typically refluxed and stirred for from about 6 hours to about 20 hours, then concentrated under reduced pressure to provide acetal intermediate (8).

Typically, a solution of intermediate (8) in an inert diluent, such as dichloromethane, in the presence of a base, such as DIPEA, is reacted with between about 1 and about 3 equivalents of compound (IV), $L^1$-$R^4$, (where $L^1$ is a leaving group such as halo, and $R^4$ is —C(O)O—$C_{1-3}$alkyl or —C(O)—$C_{1-3}$alkyl). The reaction is typically conducted at between about −20° C. and about 20° C. for between about 0.5 hours to about 12 hours. The stirred reaction is allowed to warm to room temperature. The reaction mixture is concentrated and purified to provide intermediate (9).

The acetal intermediate (9) is typically contacted with an acid, such as aqueous hydrochloric acid, and stirred for between about 30 minutes and about 2 hours. Then the excess reagent is removed. The reaction mixture is diluted with aqueous aectonitrile then lyophilized to provide a compound of formula (V).

Alternatively, compounds of formula (I) can be prepared as illustrated in Scheme E shown below:

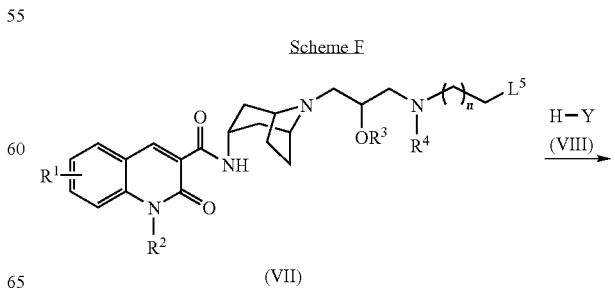

-continued

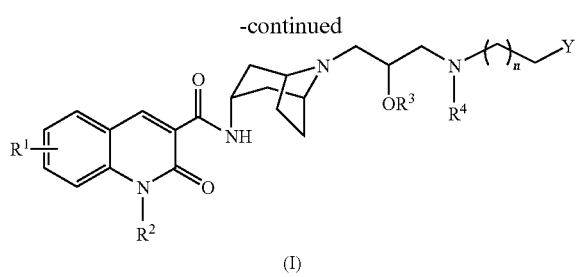

(I)

by reacting a compound of formula (VII) wherein $L^5$ is a leaving group, such as halo, with a compound of formula (VIII).

Optimal reaction conditions for the reaction of Scheme E may vary depending on the chemical properties of the reagent H—Y, as is well known to those skilled in the art.

For example, when $L^5$ is a halo leaving group, such as chloro, and H—Y is an N-linked heterocycle, the reaction is typically conducted by contacting a compound of formula (VII) with between about 1 and about 4 equivalents of reagent H—Y in an inert diluent, such as methanol, ethanol, DMF, N-methylpyrrolinone (NMP), and the like, in the presence of a base, such as N,N-diisopropylethylamine or 1,8-diazabicyclo[5.4.0]-undec-7-ene (DBU). Suitable inert diluents include nitriles, such as acetonitrile, N,N-dimethylformamide, 1,1,2,2-tetrachloroethane, tetrahydrofuran, and the like. The reaction is typically conducted at a temperature in the range of about 40° C. to about 120° C. for about 2 hours to about 24 hours, or until the reaction is substantially complete.

A compound of formula (VII) can be prepared by reducing a compound of formula (V) to an alcohol in the presence of a reducing agent, such as hydrogen and a metal catalyst, or a borohydride, such as sodium borohydride, then reacting the alcohol product with a reagent, such as phosphorus tribromide or thionyl chloride, to provide a compound of formula (VII).

Alternatively, when $R^4$ is $-S(O)_2-C_{1-3}$alkyl, a compound of formula (I) can be prepared according to Scheme F:

Scheme F

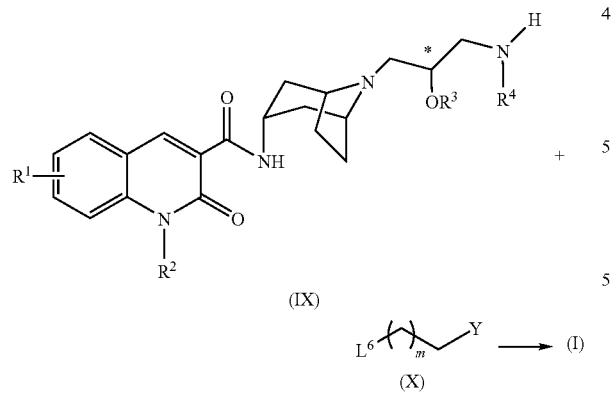

wherein $L^6$ is a leaving group, such as halo, and the asterisk denotes a chiral center. The process utilizing a compound of formula (IX) is useful for preparing compounds of formula (I) in which the stereochemistry at the carbon marked by the asterisk is specifically (R) or (S) as well as for preparing non-chiral compounds.

Typically, a compound of formula (IX) is contacted with between about 1 and about 6 equivalents of compound (X) in a polar diluent, such as methanol, ethanol, DMF, NMP, or the like, in the presence of 2 to 3 equivalents of a base, such as N,N-diisopropylethylamine, potassium carbonate, sodium hydroxide, and the like. The reaction is typically conducted at a temperature of between about 0° C. and about 120° C. for between about 12 and about 24 hours, or until the reaction is substantially complete to provide a compound of formula (I).

In an alternative method of synthesis, a compound of formula (I) can be prepared as illustrated in Scheme G:

Scheme G

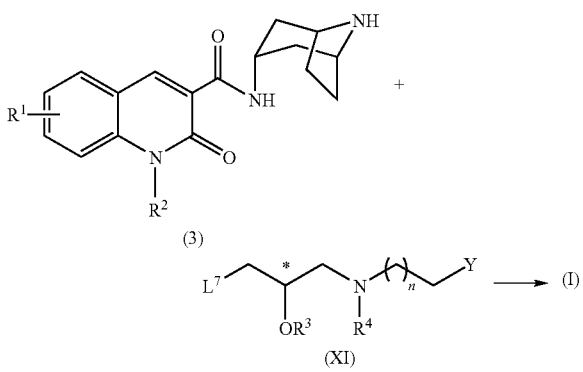

wherein $L^7$ is a leaving group, such as halo, and the asterisk denotes a chiral center.

Alternatively, a compound of formula (I) wherein $R^3$ is hydrogen, and the asterisk denotes a chiral center, can be prepared as illustrated in Scheme H:

Scheme H

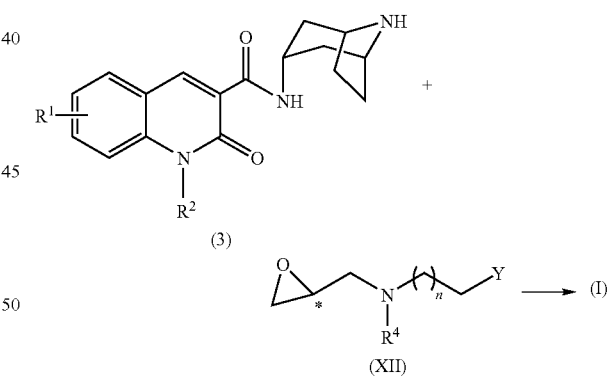

Schemes G and H are useful for preparing compounds of formulae (I) in which the stereochemistry at the center marked by the asterisk is specifically (R) or (S) as well as for preparing non-chiral compounds.

Typically, a compound of formula (3) is contacted with between about 1 and about 4 equivalents of a compound of formula (XI) in a polar diluent, such as methanol, N,N-dimethylformamide (DMF), or the like, in the presence of more than one equivalent of a base, such as N,N-diisopropylethylamine or the like. Alternatively, a compound of formula (3) is contacted with between about 1 and about 4 equivalents of a compound of formula (XII) in a polar diluent, such as methanol, N,N-dimethylformamide (DMF), or the like. The reaction is typically conducted at a temperature of between about 25° C. and about 100° C. for between about 2 and about 24 hours, or until the reaction is substantially complete to provide a compound of formula (I).

In yet another alternative process, a compound of formula (I) can be prepared according to Scheme J:

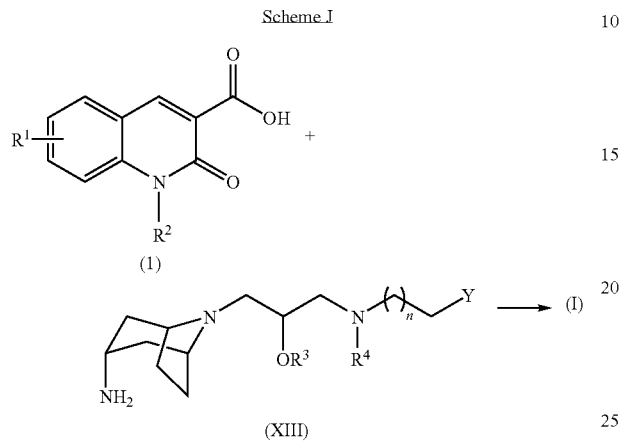

The reaction of Scheme J is typically conducted under amide coupling conditions known in the art. Typically, this reaction is conducted by converting a carboxylic acid (i.e., a compound of formula (1)) to an acid chloride by contacting compound (1) with at least one equivalent, preferably between about 1 and about 2 equivalents of an activating agent such as thionyl chloride or oxalyl chloride in an aromatic diluent, such as toluene, benzene, xylene, or the like. The reaction is typically conducted at a temperature ranging from about 80° C. to about 120° C. for about 15 minutes to about 4 hours, or until the reaction is substantially complete.

The acid chloride solution is typically added to a biphasic mixture of about 1 equivalent of the aminotropane (a compound of formula (XIII)) to form a compound of formula (I). The biphasic mixture of a compound of formula (XIII) is generally prepared by dissolving a compound of formula (XIII) in an aromatic diluent, such as toluene, and adding an aqueous solution containing an excess of base, such as sodium hydroxide or potassium hydroxide, preferably about 2 to about 10 equivalents of base.

Alternatively, the amide coupling of a compound of formula (XIII) with the carboxylic acid compound of formula (1) can be performed in the presence of a coupling agent such as 1,3 dicyclohexylcarbodiimide (DCC), 1-(3-dimethylamino-propyl)-3-ethylcarbodiimide (EDC), or benzotriazol-1-yloxytripyrrolidino-phosphonium hexafluorophosphate (PyBop), optionally combined with 1-hydroxy-7-azabenzotriazole (HOAt), as described above in Scheme A for the amide coupling of a compound of formula (III) with a carboxylic acid ($L^1$-$R^4$). In yet another alternative, the amide coupling of Scheme J can be performed by converting a compound of formula (1) to an activated ester, as described in Scheme A herein.

In yet another alternative process, when $R^4$ is —C(O)O—$C_{1-3}$alkyl or —C(O)—$C_{1-3}$alkyl a compound of formula (I) can be prepared according to Scheme K:

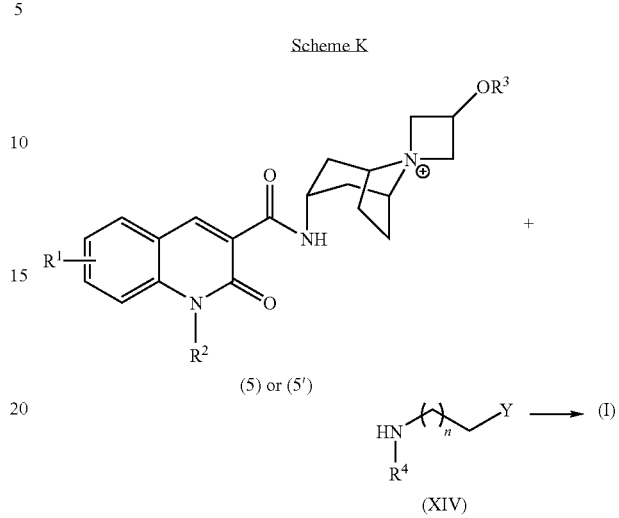

by reacting an azetidine compound of formula (5) or (5') with a compound of formula (XIV) in the presence of a strong base, such as sodium hydride. Typically, the azetidine intermediate is dissolved in a polar diluent, such as DMF, in the presence of a strong base, and contacted with between about 1 and about 8 equivalents, such as between about 1 and 3 equivalents, of the protected amine. The reaction is typically conducted at a temperature of between about 0° C. and about 100° C. for between about 12 and about 24 hours or until the reaction is substantially complete.

Reagents $L^1$-$R^4$, $L^2$-$R^2$, $L^4$-$R^3$, H—Y, compounds of formulae (IX), (X), (XI), (XII), (XIII), and (XIV), and other intermediates are readily prepared by standard procedures from common starting materials or are available commercially. Further details regarding specific reaction conditions and other procedures for preparing representative compounds of the invention or intermediates thereto are described in the examples below.

Accordingly, in a method aspect, the invention provides a process for preparing a compound of formula (I), or a pharmaceutically-acceptable salt or solvate or stereoisomer thereof, the process comprising:

(a) reacting a compound of formula (III):

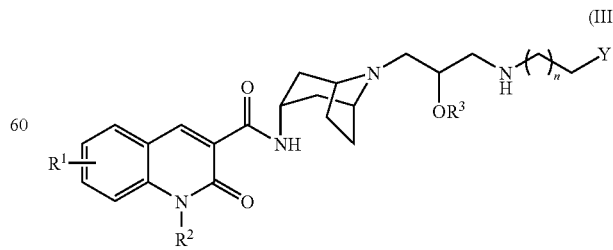

or a salt or stereoisomer or protected derivative thereof;

with a compound of formula (IV):

$$L^1\text{-}R^4 \quad (IV)$$

wherein $L^1$ is a leaving group; or (b) reacting a compound of formula (VII)

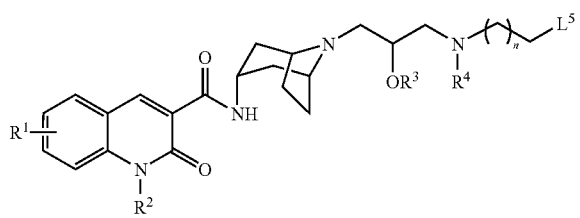

(VII)

wherein $L^5$ is a leaving group; or a salt or stereoisomer or protected derivative thereof;

with a compound of formula (VIII):

$$H\text{—}Y \quad (VIII)$$

to provide a compound of formula (I) or a pharmaceutically-acceptable salt or solvate or stereoisomer thereof.

The invention further provides a process for preparing a compound of formula (II), or a pharmaceutically-acceptable salt or solvate or stereoisomer thereof, the process comprising:

reacting a compound of formula (V):

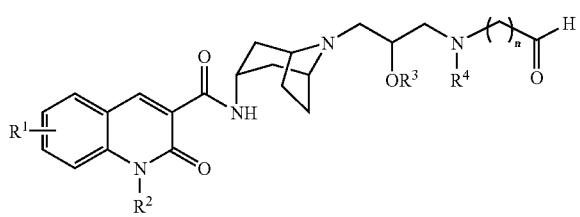

(V)

or a salt, hydrate, stereoisomer or protected derivative thereof;

with a compound of formula (VI):

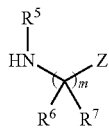

(VI)

in the presence of a reducing agent to provide a compound of formula (II) or a pharmaceutically-acceptable salt or solvate or stereoisomer thereof.

In other embodiments, this invention is directed to the other processes described herein; and to the products prepared by any of the processes described herein.

The invention further provides a compound of formula (III), or a salt or stereoisomer or protected derivative thereof. In a specific aspect, the invention provides a compound of formula (III), or a salt or stereoisomer or protected derivative thereof, wherein Y is a moiety of formula (a) and $R^1$, $R^2$, $R^3$, and n are as defined herein.

Pharmaceutical Compositions

The quinolinone-carboxamide compounds of the invention are typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of the invention are typically prepared by thoroughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

In a preferred embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (such as, for example, cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, a compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following formulations illustrate representative pharmaceutical compositions of the present invention:

FORMULATION EXAMPLE A

Hard gelatin capsules for oral administration are prepared as follows:

| Ingredients | Amount |
| --- | --- |
| Compound of the invention | 50 mg |
| Lactose (spray-dried) | 200 mg |
| Magnesium stearate | 10 mg |

Representative Procedure: The ingredients are thoroughly blended and then loaded into a hard gelatin capsule (260 mg of composition per capsule).

FORMULATION EXAMPLE B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 2 mg |

Representative Procedure: The ingredients are thoroughly blended and then passed through a No. 45 mesh U.S. sieve and loaded into a hard gelatin capsule (200 mg of composition per capsule).

FORMULATION EXAMPLE C

Capsules for oral administration are prepared as follows:

| Ingredients | Amount |
| --- | --- |
| Compound of the invention | 10 mg |
| Polyoxyethylene sorbitan monooleate | 50 mg |
| Starch powder | 250 mg |

Representative Procedure: The ingredients are thoroughly blended and then loaded into a gelatin capsule (310 mg of composition per capsule).

FORMULATION EXAMPLE D

Tablets for oral administration are prepared as follows:

| Ingredients | Amount |
| --- | --- |
| Compound of the invention | 5 mg |
| Starch | 50 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The active ingredient, starch and cellulose are passed through a No. 45 mesh U.S. sieve and mixed thoroughly. The solution of polyvinylpyrrolidone is mixed with the resulting powders, and this mixture is then passed through a No. 14 mesh U.S. sieve. The granules so produced are dried at 50-60° C. and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

FORMULATION EXAMPLE E

Tablets for oral administration are prepared as follows:

| Ingredients | Amount |
| --- | --- |
| Compound of the invention | 25 mg |
| Microcrystalline cellulose | 400 mg |
| Silicon dioxide fumed | 10 mg |
| Stearic acid | 5 mg |

Representative Procedure: The ingredients are thoroughly blended and then compressed to form tablets (440 mg of composition per tablet).

FORMULATION EXAMPLE F

Single-scored tablets for oral administration are prepared as follows:

| Ingredients | Amount |
| --- | --- |
| Compound of the invention | 15 mg |
| Cornstarch | 50 mg |
| Croscarmellose sodium | 25 mg |
| Lactose | 120 mg |
| Magnesium stearate | 5 mg |

Representative Procedure: The ingredients are thoroughly blended and compressed to form a single-scored tablet (215 mg of compositions per tablet).

FORMULATION EXAMPLE G

A suspension for oral administration is prepared as follows:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 10 mg of active ingredient per 10 mL of suspension.

FORMULATION EXAMPLE H

A dry powder for administration by inhalation is prepared as follows:

| Ingredients | Amount |
| --- | --- |
| Compound of the invention | 1.0 mg |
| Lactose | 25 mg |

Representative Procedure: The active ingredient is micronized and then blended with lactose. This blended mixture is then loaded into a gelatin inhalation cartridge. The contents of the cartridge are administered using a powder inhaler.

FORMULATION EXAMPLE I

A dry powder for administration by inhalation in a metered dose inhaler is prepared as follows:

Representative Procedure: A suspension containing 5 wt. % of a compound of the invention and 0.1 wt. % lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

FORMULATION EXAMPLE J

An injectable formulation is prepared as follows:

| Ingredients | Amount |
| --- | --- |
| Compound of the invention | 0.2 g |
| Sodium acetate buffer solution (0.4 M) | 40 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

FORMULATION EXAMPLE K

Capsules for oral administration are prepared as follows:

| Ingredients | Amount |
| --- | --- |
| Compound of the Invention | 4.05 mg |
| Microcrystalline cellulose (Avicel PH 103) | 259.2 mg |
| Magnesium stearate | 0.75 mg |

Representative Procedure: The ingredients are thoroughly blended and then loaded into a gelatin capsule (Size #1, White, Opaque) (264 mg of composition per capsule).

FORMULATION EXAMPLE L

Capsules for oral administration are prepared as follows:

| Ingredients | Amount |
| --- | --- |
| Compound of the Invention | 8.2 mg |
| Microcrystalline cellulose (Avicel PH 103) | 139.05 mg |
| Magnesium stearate | 0.75 mg |

Representative Procedure: The ingredients are thoroughly blended and then loaded into a gelatin capsule (Size #1, White, Opaque) (148 mg of composition per capsule).

It will be understood that any form of the compounds of the invention, (i.e. free base, pharmaceutical salt, or solvate) that is suitable for the particular mode of administration, can be used in the pharmaceutical compositions discussed above.

Utility

The quinolinone-carboxamide compounds of the invention are 5-$HT_4$ receptor agonists and therefore are expected to be useful as therapeutic agents for treating medical conditions mediated by 5-$HT_4$ receptors or associated with 5-$HT_4$ receptor activity, i.e. medical conditions which are ameliorated by treatment with a 5-$HT_4$ receptor agonist. Such medical conditions include, but are not limited to, irritable bowel syndrome (IBS), chronic constipation, functional dyspepsia, delayed gastric emptying, gastroesophageal reflux disease (GERD), gastroparesis, diabetic and idiopathic gastropathy, post-operative ileus, intestinal pseudo-obstruction, and drug-induced delayed transit. In addition, it has been suggested that some 5-$HT_4$ receptor agonist compounds may be used in the treatment of central nervous system disorders including cognitive disorders, behavioral disorders, mood disorders, and disorders of control of autonomic function.

In particular, the compounds of the invention are expected to be useful for treating disorders of the GI tract caused by reduced motility in mammals, including humans. Such GI motility disorders include, by way of illustration, chronic constipation, irritable bowel syndrome, diabetic and idiopathic gastroparesis, and functional dyspepsia.

When used to treat disorders of reduced motility of the GI tract or other conditions mediated by 5-$HT_4$ receptors, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by 5-$HT_4$ receptors will range from about 0.0007 to about 20 mg/kg/day of active agent, preferably from about 0.0007 to about 1 mg/kg/day. For an average 70 kg human, this would amount to from about 0.05 to about 70 mg per day of active agent.

In one aspect of the invention, the compounds of the invention are used to treat chronic constipation. When used to treat chronic constipation, the compounds of the invention will typically be administered orally in a single daily dose or in multiple doses per day. Preferably, the dose for treating chronic constipation will range from about 0.05 to about 70 mg per day.

In another aspect of the invention, the compounds of the invention are used to treat irritable bowel syndrome. When used to treat constipation-predominant irritable bowel syndrome, the compounds of the invention will typically be administered orally in a single daily dose or in multiple doses per day. Preferably, the dose for treating constipation-predominant irritable bowel syndrome will range from about 0.05 to about 70 mg per day.

In another aspect of the invention, the compounds of the invention are used to treat diabetic gastroparesis. When used to treat diabetic gastroparesis, the compounds of the invention will typically be administered orally in a single daily dose or in multiple doses per day. Preferably, the dose for treating diabetic gastroparesis will range from about 0.05 to about 70 mg per day.

In yet another aspect of the invention, the compounds of the invention are used to treat functional dyspepsia. When used to treat functional dyspepsia, the compounds of the invention will typically be administered orally in a single daily dose or in multiple doses per day. Preferably, the dose for treating functional dyspepsia will range from about 0.05 to about 70 mg per day.

The invention also provides a method of treating a mammal having a disease or condition associated with 5-HT$_4$ receptor activity, the method comprising administering to the mammal a therapeutically effective amount of a compound of the invention or of a pharmaceutical composition comprising a compound of the invention.

Since compounds of the invention are 5-HT$_4$ receptor agonists, such compounds are also useful as research tools for investigating or studying biological systems or samples having 5-HT$_4$ receptors, or for discovering new 5-HT$_4$ receptor agonists. Moreover, since compounds of the invention exhibit binding selectivity for 5-HT$_4$ receptors as compared with binding to receptors of other 5-HT subtypes, particularly 5-HT$_3$ receptors, such compounds are particularly useful for studying the effects of selective agonism of 5-HT$_4$ receptors in a biological system or sample. Any suitable biological system or sample having 5-HT$_4$ receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like.

In this aspect of the invention, a biological system or sample comprising a 5-HT$_4$ receptor is contacted with a 5-HT$_4$ receptor-agonizing amount of a compound of the invention. The effects of agonizing the 5-HT$_4$ receptor are then determined using conventional procedures and equipment, such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of analogs of guanosine triphosphate (GTP), such as [$^{35}$S]GTPγS (guanosine 5'-O-(γ-thio) triphosphate) or GTP-Eu, into isolated membranes via receptor catalyzed exchange of GTP analogs for GDP analogs, ligand-mediated changes in free intracellular calcium ions (measured, for example, with a fluorescence-linked imaging plate reader or FLIPR® from Molecular Devices, Inc.), and measurement of mitogen activated protein kinase (MAPK) activation. A compound of the invention may agonize or increase the activation of 5-HT$_4$ receptors in any of the functional assays listed above, or assays of a similar nature. A 5-HT$_4$ receptor-agonizing amount of a compound of the invention will typically range from about 1 nanomolar to about 1000 nanomolar.

Additionally, the compounds of the invention can be used as research tools for discovering new 5-HT$_4$ receptor agonists. In this embodiment, 5-HT$_4$ receptor binding or functional data for a test compound or a group of test compounds is compared to the 5-HT$_4$ receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to be potent agonists of the 5-HT$_4$ receptor and to exhibit substantial selectivity for the 5-HT$_4$ receptor subtype over the 5-HT$_3$ receptor subtype in radioligand binding assays. In addition, representative compounds have been shown not to exhibit an unacceptable level of inhibition of the potassium ion current in an in vitro voltage-clamp model using isolated whole cells expressing the hERG cardiac potassium channel. The voltage-clamp assay is an accepted pre-clinical method of assessing the potential for pharmaceutical agents to change the pattern of cardiac repolarization, specifically to cause, so-called QT prolongation, which has been associated with cardiac arrhythmia. (Cavero et al., *Opinion on Pharmacotherapy*, 2000, 1, 947-73, Fermini et al., *Nature Reviews Drug Discovery*, 2003, 2, 439-447) Accordingly, pharmaceutical compositions comprising compounds of the invention are expected to have an acceptable cardiac profile.

These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

Boc=tert-butoxycarbonyl
(Boc)$_2$O=di-tert-butyl dicarbonate
DCM=dichloromethane
DMF=N,N-dimethylformamide
DMSO=dimethyl sulfoxide
EtOAc=ethyl acetate
mCPBA=m-chloroperbenzoic acid
MeCN=acetonitrile
MTBE=tert-butyl methyl ether
PyBOP=benzotriazol-1-yloxytripyrrolidino-phosphonium hexafluorophosphate
R$_f$=retention factor
RT=room temperature
TFA=trifluoroacetic acid
THF=tetrahydrofuran Reagents (including some secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (300 MHz) under standard observation conditions. Mass spectrometric identification of compounds was performed by an electrospray ionization method (ESMS) with a Perkin Elmer instrument (PE SCIEX API 150 EX).

General Protocol for Analytical HPLC

Crude compounds were dissolved in 50% MeCN/$H_2O$ (with 0.1% TFA) at 0.5-1.0 mg/mL concentration, and analyzed using the following conditions:

| Column: | Zorbax Bonus-RP (3.5 μm of particle size, 2.1 × 50 mm) |
|---|---|
| Flow rate: | 0.5 mL/min |
| Mobile Phases: | A = 90% MeCN/10% $H_2O$/0.1% TFA |
| | B = 98% $H_2O$/2% MeCN/0.1% TFA |
| Gradient: | 10% A/90% B (0-0.5 min); |
| | 10% A/90% B to 50% A/50% B (linear, 0.5-5 min) |
| Detector wavelength: | 214, 254, and 280 nm. |

Alternative conditions, when used, are indicated explicitly.

General Protocol for Preparative HPLC Purification

Crude compounds were dissolved in 50% acetic acid in water at 50-100 mg/mL concentration, filtered, and fractionated using the following procedure:

| Column: | YMC Pack-Pro C18 (50 a × 20 mm; ID = 5 μm) |
|---|---|
| Flow rate: | 40 mL/min |
| Mobile Phases: | A = 90% MeCN/10% $H_2O$/0.1% TFA |
| | B = 98% $H_2O$/2% MeCN/0.1% TFA |
| Gradient: | 10% A/90% B to 50% A/50% B over 30 min (linear) |
| Detector wavelength: | 214 nm. |

Preparation of Secondary Amines (such as Compounds of Formula (VIII), H—Y)

Preparation of Various Secondary Amines Used as Intermediates in the Synthesis of a compound of formula (I) are described below.

Thiomorpholine-1,1-dioxide was prepared from thiomorpholine by protection of the secondary amine to N-Boc thiomorpholine ((Boc)$_2$O, MeOH), oxidation to sulfone (mCPBA, $CH_2Cl_2$, 0° C.), and deprotection of the N-Boc group to provide the free amine ($CF_3CO_2H$, $CH_2Cl_2$). (m/z): [M+H]$^+$ calcd for $C_4H_9NO_2S$, 136.04; found, 135.9.

The N-sulfonyl derivatives of piperazine were prepared from N-Boc piperazine by reacting with respective sulfonyl chloride (iPr$_2$NEt, $CH_2Cl_2$, 0° C.), and deprotecting the N-Boc group ($CF_3CO_2H$, $CH_2Cl_2$). 1-Methanesulfonyl-piperazine: $^1$H-NMR ($CDCl_3$; neutral): δ (ppm) 3.1 (t, 4H), 2.9 (t, 4H), 2.7 (s, 3H). 1-(Methylsulfonyl)methanesulfonyl-piperazine: $^1$H-NMR ($CD_3OD$): δ (ppm) 2.90 (s, 3H), 3.02 (m, 4H), 3.38 (m, 4H), 4.61 (s, 2H). Methanesulfonylpiperazine was also prepared by reacting methanesulfonyl chloride with excess piperazine (>2 equivalents) in water.

The racemic or single chiral isomer forms of 3-acetylaminopyrrolidine were prepared by treating N$^1$-Boc-3-aminopyrrolidine (racemate, 3R, or 3S) with acetyl chloride (iPr$_2$NEt, $CH_2Cl_2$, 0° C.), and deprotecting the N-Boc group ($CF_3CO_2H$, $CH_2Cl_2$). 3-(Acetamido)pyrrolidine: $^1$H-NMR (DMSO-$d_6$; TFA salt): δ (ppm) 4.2 (quin, 1H), 3.3-3.1 (m, 3H), 2.9 (m, 1H), 2.0 (m, 1H), 1.8 (br s, 4H).

3-((R)-2-Hydroxypropionamido)pyrrolidine was prepared after amidation of N$^1$-Boc-3-aminopyrrolidine (L-lactic acid, PyBOP, DMF, RT), and deprotection of N-Boc group ($CF_3CO_2H$, $CH_2Cl_2$). (m/z): [M+H]$^+$ calcd for $C_7H_{14}N_2O_2$, 159.11; found, 159.0. $^1$H-NMR ($CD_3OD$; TFA salt): δ (ppm) 4.4 (quin, 1H), 4.1 (q, 1H), 3.5-3.4 (m, 2H), 3.3-3.2 (m, 2H), 2.3 (m, 1H), 2.0 (m, 1H), 1.3 (d, 3H).

The N$^3$-alkanesulfonyl derivatives of (3R)-aminopyrrolidine were obtained by treating N$^1$-Boc-(3R)-aminopyrrolidine with propionylsulfonyl chloride or cyclohexylmethylsulfonyl chloride (i-Pr$_2$NEt, $CH_2Cl_2$, 0° C.), and deprotecting N-Boc group ($CF_3CO_2H$, $CH_2Cl_2$).

3-(N-Acetyl-N-methylamido)piperidine was prepared from N$^3$-Cbz protected 3-amino-piperidine-1-carboxylic acid t-butyl ester (De Costa, B., et al. *J. Med. Chem.* 1992, 35, 4334-43) after four synthetic steps: i) MeI, n-BuLi, THF, −78° C. to rt; ii) $H_2$ (1 atm), 10% Pd/C, EtOH; iii) AcCl, i-Pr$_2$NEt, $CH_2Cl_2$; iv) $CF_3CO_2H$, $CH_2Cl_2$. m/z: [M+H]$^+$ calcd for $C_8H_{16}N_2O$: 157.13; found, 157.2. $^1$H-NMR ($CD_3OD$; TFA salt): δ (ppm) 4.6 (m, 1H), 3.3 (m, 1H), 3.2 (m, 1H), 3.0 (m, 1H), 2.9 (s, 3H), 2.8 (m, 1H), 2.0 (s, 3H), 1.9-1.7 (m, 4H).

3-(N-Acetyl-amido)piperidine was prepared from 3-amino-piperidine-1-carboxylic acid tert-butyl ester after N-acetylation and deprotection of the N-Boc group: i) AcCl, i-Pr$_2$NEt, $CH_2Cl_2$; ii) $CF_3CO_2H$, $CH_2Cl_2$. $^1$H-NMR ($CD_3OD$; TFA salt): δ (ppm) 3.9 (m, 1H), 3.3 (dd, 1H), 3.2 (m, 1H), 2.9 (dt, 1H), 2.75 (dt, 1H), 2.0-1.9 (m, 2H), 1.9 (s, 3H), 1.8-1.4 (m, 2H).

The N$^3$-alkanesulfonyl derivatives of 3-aminopiperidine were synthesized by reacting the chiral or racemic forms of 3-amino-piperidine-1-carboxylic acid tert-butyl ester with the respective alkanesulfonyl chloride (i-Pr$_2$NEt, $CH_2Cl_2$) and deprotecting the N-Boc group ($CF_3CO_2H$, $CH_2Cl_2$). (3S)-3-(ethanesulfonylamido)piperidine: $^1$H-NMR ($CD_3OD$): δ (ppm) 1.29 (t, 3H, $J_1$=7.4 Hz), 1.50-1.80 (m, 2H), 1.90-2.10 (m, 2H), 2.89 (m, 2H), 3.05 (q, 2H, $J_1$=7.4 Hz), 3.27 (m, 2H), 3.40 (d of d(br), 1H), 3.52 (m, 1H). 3S-Methylsulfonylmethanesulfonylamido-piperidine: $^1$H-NMR ($CD_3OD$): δ (ppm) 2.13-2.30 (m, 2H), 2.40-2.57 (m, 2H), 2.98 (m, 2H), 3.15 (s, 3H), 3.21 (m, 2H), 3.30 (br d, 1H), 3.74 (m, 1H).

3-(Methylamino)-1-acetylpyrrolidine was prepared from 3-(methylamino)-1-benzylpyrrolidine (TCI America) after four steps: i) (Boc)$_2$O, MeOH, rt; ii) $H_2$ (1 atm), 10% Pd/C, EtOH; iii) AcCl, i-Pr$_2$NEt, $CH_2Cl_2$; iv) $CF_3CO_2H$, $CH_2Cl_2$. (m/z): [M+H]$^+$ calcd for $C_7H_{14}N_2O$: 143.12; found, 143.0.

3-(Methylamino)-1-(methanesulfonyl)pyrrolidine was prepared from 3-(methylamino)-1-benzylpyrrolidine after four steps: i) (Boc)$_2$O, MeOH, rt; ii) $H_2$ (1 atm), 10% Pd/C, EtOH; iii) $CH_3SO_2Cl$, i-Pr$_2$NEt, $CH_2Cl_2$; iv) $CF_3CO_2H$, $CH_2Cl_2$. (m/z): [M+H]$^+$ calcd for $C_6H_{14}N_2O_2S$: 179.08; found, 179.2. 3R-Methylamino-1-(methanesulfonyl)pyrrolidine was prepared in a similar manner from (3R)-(methylamino)-1-benzylpyrrolidine.

Derivatives of tetrahydro-3-thiophenamine-1,1-dioxide were prepared following the protocol of Loev, B. *J. Org. Chem.* 1961, 26, 4394-9 by reacting 3-sulfolene with a requisite primary amine in methanol (cat. KOH, rt). N-Methyl- 3-tetrahydrothiopheneamine-1,1-dioxide (TFA salt): $^1$H-NMR (DMSO-d$_6$): δ (ppm) 9.4 (br s, 2H), 4.0-3.8 (quin, 1H), 3.6-3.5 (dd, 1H), 3.4-3.3 (m, 1H), 3.2-3.1 (m, 2H), 2.5 (s, 3H), 2.4 (m, 1H), 2.1 (m, 1H). N-2-(1-hydroxy)ethyl-3-tetrahydrothiopheneamine-1,1-dioxide: (m/z): [M+H]$^+$ calcd for C$_6$H$_{13}$NO$_3$S: 180.07; found, 180.2.

N-Methyl-tetrahydro-2H-thiopyran-4-amine-1,1-dioxide was prepared from tetrahydro-4H-thiopyran-4-one: i) MeNH$_2$, NaBH$_4$; ii) (Boc)$_2$O, MeOH; iii) mCPBA, CH$_2$Cl$_2$, 0° C.; iv) CF$_3$CO$_2$H, CH$_2$Cl$_2$. (m/z): [M+H]$^+$ calcd for C$_6$H$_{13}$NO$_2$S 164.07; found, 164.9. $^1$H-NMR (CD$_3$OD; TFA salt): δ (ppm) 3.4-3.1 (m, 5H), 2.7 (s, 3H), 2.4 (br d, 2H), 2.1 (br m, 2H).

1-Acetyl-3-(methylamino)piperidine was prepared from N$^3$-Cbz protected 3-methylamino-piperidine: i) AcCl, i-Pr$_2$NEt, CH$_2$Cl$_2$; ii) H$_2$ (1 atm), 10% Pd/C, EtOH. $^1$H-NMR (CD$_3$OD): δ (ppm) 4.0 (m, 1H), 3.6 (m, 1H), 3.4-3.2 (m, 2H), 3.0 (m, 1H), 2.6 (s, 3H), 2.1 (s, 3H), 1.8-1.6 (m, 4H).

1-(Methanesulfonyl)-3-(methylamino)piperidine was prepared from N$^3$-Cbz protected 3-methylamino-piperidine: i) CH$_3$SO$_2$Cl, i-Pr$_2$NEt, CH$_2$Cl$_2$; ii) H$_2$ (1 atm), 10% Pd/C, EtOH. (m/z): [M+H]$^+$ calcd for C$_7$H$_{16}$N$_2$O$_2$S 193.10; found, 193.0. $^1$H-NMR (DMSO-d$_6$; TFA salt): δ (ppm) 3.4 (dd, 1H), 3.2 (m, 2H), 3.10 (s, 3H), 3.0-2.9 (m, 2H), 2.8 (s, 3H), 1.85-1.75 (m, 2H), 1.6-1.4 (m, 2H).

Proline dimethylamide, and iminodiacetonitrile were purchased from Bachem, and Aldrich, respectively.

The N-derivatives of piperazine such as 1-(methoxycarbonyl)piperazine, 1-(dimethylaminocarbonyl)piperazine, and 1-(dimethylaminosulfonyl)piperazine were prepared by reacting piperazine with methylchloroformate, dimethylaminochoroformate, or dimethylaminosulfamoyl chloride, respectively.

1-Methylamino-2-methylsulfonylethane was obtained by reacting methylamine with methyl vinyl sulfone in methanol. N-[2-(2-methoxyethylamino)ethyl], N-methyl-methanesulfonamide was synthesized starting from partially N-Boc protected ethanediamine after four steps of reactions in a sequence as follows: i) methylsulfonyl chloride, triethylamine; ii) MeI, Cs$_2$CO$_3$; iii) NaH, 1-bromo-2-methoxyethane; iv) CF$_3$CO$_2$H.

Isonipecotamide(piperidine-4-carboxamide), and proline amide were purchased from Aldrich. 2-Hydroxymethylmorpholine was available from Tyger Scientific Product.

Methyl 4-piperidinylcarbamate was prepared from the reaction of N$_1$-Boc protected 4-aminopiperidine with methylchloroformate followed by the deprotection of the N-Boc group.

4-Piperidinol-dimethylcarbamate, and N-dimethyl-N'-(3-piperidinyl)urea were prepared by reacting dimethylcarbamoyl chloride with N-Boc protected 4-piperidinol or N$_1$-Boc-3-aminopiperidine, respectively.

3-(Methylamino)-1-(dimethylaminosulfonyl)pyrrolidine was obtained by reacting 3-(N-methyl-N-Boc-amino)pyrrolidine with dimethylsulfamoyl chloride.

2-(3-Pyrrolidinyl)isothiazolidine-1,1-dioxide was synthesized by treating N$_1$-Boc protected 3-aminopyrrolidine with 3-chloropropylsulfonyl chloride in the presence of triethylamine, and followed by TFA treatment for the deprotection of the Boc group.

Example 1

Synthesis of 1-Isopropyl-2-oxo-1,2-dihydroquinoline-3-carboxylic acid (1S,3R,5R)-[8-(2-hydroxy-3-{[2-(2-hydroxyethoxy)ethyl]methanesulfonylamino}propyl)-8-azabicyclo[3.2.1]oct-3-yl]amide

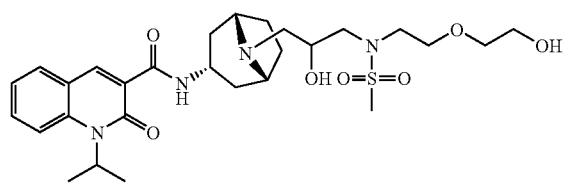

a. Preparation of 8-benzyl-8-azabicyclo[3.2.1]octan-3-one

Concentrated hydrochloric acid (30 mL) was added to a heterogeneous solution of 2,5-dimethoxy tetrahydrofuran (82.2 g, 0.622 mol) in water (170 mL) while stirring. In a separate flask cooled to 0° C. (ice bath), concentrated hydrochloric acid (92 mL) was added slowly to a solution of benzyl amine (100 g, 0.933 mol) in water (350 mL). The 2,5-dimethoxytetrahydrofuran solution was stirred for approximately 20 min, diluted with water (250 mL), and then the benzyl amine solution was added, followed by the addition of a solution of 1,3-acetonedicarboxylic acid (100 g, 0.684 mol) in water (400 mL) and then the addition of sodium hydrogen phosphate (44 g, 0.31 mol) in water (200 mL). The pH was adjusted from pH 1 to pH ~4.5 using 40% NaOH. The resulting cloudy and pale yellow solution was stirred overnight. The solution was then acidified to pH 3 from pH 7.5 using 50% hydrochloric acid, heated to 85° C. and stirred for 2 hours. The solution was cooled to room temperature, basified to pH 12 using 40% NaOH, and extracted with DCM (3×500 mL). The combined organic layers were washed with brine, dried (MgSO$_4$), filtered and concentrated under reduced pressure to afford the crude title intermediate as a viscous brown oil (52 g).

To a solution of the crude intermediate in methanol (1000 mL) was added di-tert-butyl dicarbonate (74.6 g, 0.342 mol) at 0° C. The solution was allowed to warm to room temperature and stirred overnight. The methanol was removed under reduced pressure and the resulting oil was dissolved in dichloromethane (1000 mL). The intermediate was extracted into 1 M H$_3$PO$_4$ (1000 mL) and washed with dichloromethane (3×250 mL) The aqueous layer was basified to pH 12 using aqueous NaOH, and extracted with dichloromethane (3×500 mL). The combined organic layers were dried (MgSO$_4$), filtered and concentrated under reduced pressure to produce the title intermediate as a viscous, light brown oil. $^1$H-NMR (CDCl$_3$) δ (ppm) 7.5-7.2 (m, 5H, C$_6$H$_5$), 3.7 (s, 2H, CH$_2$Ph), 3.45 (broad s, 2H, CH—NBn), 2.7-2.6 (dd, 2H, CH$_2$CO), 2.2-2.1 (dd, 2H, CH$_2$CO), 2.1-2.0 (m, 2H, CH$_2$CH$_2$), 1.6 (m, 2H, CH$_2$CH$_2$). (m/z): [M+H]$^+$ calcd for C$_{14}$H$_{17}$NO 216.14; found, 216.0.

b. Preparation of 3-oxo-8-azabicyclo[3.2.1]octane-8-carboxylic acid tert-butyl ester To a solution of 8-benzyl-8-azabicyclo[3.2.1]octan-3-one (75 g, 0.348 mol) in EtOAc (300 mL) was added a solution of di-tert-butyl dicarbonate (83.6 g, 0.383 mol, 1.1 eq) in EtOAc (300 mL). The resulting solution and rinse (100 mL EtOAc) was added to a 1 L Parr hydrogenation vessel containing 23 g of palladium hydroxide (20 wt. % Pd, dry basis, on carbon, ~50% wet with water; e.g. Pearlman's catalyst) under a stream of nitrogen. The reaction vessel was degassed (alternating vacuum and $N_2$ five times) and pressurized to 60 psi of $H_2$ gas. The reaction solution was agitated for two days and recharged with $H_2$ as needed to keep the $H_2$ pressure at 60 psi until the reaction was complete as monitored by silica thin layer chromatography. The solution was then filtered through a pad of Celite® and concentrated under reduced pressure to yield the title intermediate quantitatively as a viscous, yellow to orange oil. It was used in the next step without further treatment. $^1$H NMR (CDCl$_3$) δ(ppm) 4.5 (broad, 2H, CH—NBoc), 2.7 (broad, 2H, CH$_2$CO), 2.4-2.3 (dd, 2H, CH$_2$CH$_2$), 2.1 (broad m, 2H, CH$_2$CO), 1.7-1.6 (dd, 2H, CH$_2$CH$_2$), 1.5 (s, 9H, (CH$_3$)$_3$COCON)).

c. Preparation of (1S,3R,5R)-3-amino-8-azabicyclo [3.2.1]octane-8-carboxylic acid tert-butyl ester To a solution of the product of the previous step (75.4 g, 0.335 mol) in methanol (1 L) was added ammonium formate (422.5 g, 6.7 mol), water (115 mL) and 65 g of palladium on activated carbon (10% on dry basis, ~50% wet with water; Degussa type E101NE/W) under a stream of $N_2$ while stirring via mechanical stirrer. After 24 and 48 hours, additional portions of ammonium formate (132 g, 2.1 mol) were added each time. Once reaction progression ceased, as monitored by anal. HPLC, Celite® (>500 g) was added and the resulting thick suspension was filtered and then the collected solid was rinsed with methanol (~500 mL). The filtrates were combined and concentrated under reduced pressure until all methanol had been removed. The resulting cloudy, biphasic solution was then diluted with 1M phosphoric acid to a final volume of ~1.5 to 2.0 L at pH 2 and washed with dichloromethane (3×700 mL). The aqueous layer was basified to pH 12 using 40% aq. NaOH, and extracted with dichloromethane (3×700 mL). The combined organic layers were dried over MgSO$_4$, filtered, and concentrated by rotary evaporation, then high-vacuum leaving 52 g (70%) of the title intermediate, commonly N-Boc-endo-3-aminotropane, as a white to pale yellow solid. The isomer ratio of endo to exo amine of the product was >99 based on $^1$H-NMR analysis (>96% purity by analytical HPLC). $^1$H NMR (CDCl$_3$) δ (ppm) 4.2-4.0 (broad d, 2H, CHNBoc), 3.25 (t, 1H, CHNH$_2$), 2.1-2.05 (m, 4H), 1.9 (m, 2H), 1.4 (s, 9H, (CH$_3$)$_3$OCON), 1.2-1.1 (broad, 2H). (m/z): [M+H]$^+$ calcd for C$_{12}$H$_{22}$N$_2$O$_2$ 227.18; found, 227.2. Analytical HPLC (isocratic method; 2:98 (A:B) to 90:10 (A:B) over 5 min): retention time=3.68 min.

d. Preparation of 1-isopropyl-2-oxo-1,2-dihydroquinoline-3-carboxylic acid

Acetone (228.2 mL, 3.11 mol) was added to a stirred suspension of 2-aminophenylmethanol (255.2 g, 2.07 mol) and acetic acid (3.56 mL, 62 mmol) in water (2 L) at room temperature. After 4 h, the suspension was cooled to 0° C. and stirred for an additional 2.5 h and then filtered. The solid was collected and washed with water and the wet solid cooled and dried by lyophilisation to yield 2,2-dimethyl-1,4-dihydro-2H-benzo[1,3]oxazine (332.2 g, 98%) as an off-white solid. $^1$H NMR (CDCl$_3$; 300 MHz): 1.48 (s, 6H, C(CH$_3$)$_2$), 4.00 (bs, 1H, NH), 4.86 (s, 2H, CH$_2$), 6.66 (d, 1H, ArH), 6.81 (t, 1H, Ar H), 6.96 (d, 1H, ArH), 7.10 (t, 1H, ArH).

A solution of 2,2,-dimethyl-1,4-dihydro-2H-benzo[1,3] oxazine (125 g, 0.77 mol) in THF (1 L) was filtered through a scintillation funnel and then added dropwise via an addition funnel, over a period of 2.5 h, to a stirred solution of 1.0 M LiAlH$_4$ in THF (800 mL) at 0° C. The reaction was quenched by slow portionwise addition of Na$_2$SO$_4$ 10H$_2$O (110 g), over a period of 1.5 h, at 0° C. The reaction mixture was stirred overnight, filtered and the solid salts were washed thoroughly with THF. The filtrate was concentrated under reduced pressure to yield 2-isopropylaminophenylmethanol (120 g, 95%) as a yellow oil. $^1$H NMR (CDCl$_3$; 300 MHz): 1.24 (d, 6H, CH(CH$_3$)$_2$), 3.15 (bs, 1H, OH), 3.61 (sept, 1H, CH(CH$_3$)$_2$), 4.57 (s, 2H, CH$_2$), 6.59 (t, 1H, ArH), 6.65 (d, 1H, ArH), 6.99 (d, 1H, ArH), 7.15 (t, 1H, ArH).

Manganese dioxide (85% 182.6 g, 1.79 mol) was added to a stirred solution of 2-isopropylaminophenylmethanol (118 g, 0.71 mol) in toluene (800 mL) and the reaction mixture was heated to 117° C. for 4 h. The reaction mixture was allowed to cool to room temperature overnight and then filtered through a pad of Celite which was eluted with toluene. The filtrate was concentrated under reduced pressure to yield 2-isopropylaminobenzaldehyde (105 g, 90%) as an orange oil. $^1$H NMR (CDCl$_3$; 300 MHz): 1.28 (d, 6H, CH(CH$_3$)$_2$), 3.76 (sept, 1H, CH(CH$_3$)$_2$), 6.65 (t, 1H, ArH), 6.69 (d, 1H, ArH), 7.37 (d, 1H, ArH), 7.44 (t, 1H, ArH), 9.79 (s, 1H, CHO).

2,2-Dimethyl-[1,3]dioxane-4,6-dione, commonly Meldrum's acid, (166.9 g, 1.16 mol) was added to a stirred solution of 2-isopropylaminobenzaldehyde (105 g, 0.64 mol), acetic acid (73.6 mL, 1.29 mol) and ethylenediamine (43.0 mL, 0.64 mol) in methanol (1 L) at 0° C. The reaction mixture was stirred for 1 h at 0° C. and then at room temperature overnight. The resulting suspension was filtered and the solid washed with methanol and collected to yield the title intermediate, 1-isopropyl-2-oxo-1,2-dihydroquinoline-3-carboxylic acid (146 g, 98%) as an off-white solid. $^1$H NMR (CDCl$_3$; 300 MHz): 1.72 (d, 6H, CH(CH$_3$)$_2$), 5.50 (bs, 1H, CH(CH$_3$)$_2$), 7.44 (t, 1H, ArH), 7.75-7.77 (m, 2H, ArH), 7.82 (d, 1H, ArH), 8.89 (s, 1H, CH).

e. Preparation of (1S,3R,5R)-3-[1-isopropyl-2-oxo-1, 2-dihydroquinoline-3-carbonyl)amino]-8-azabicyclo [3.2.1]octane-8-carboxylic acid tert-butyl ester Thionyl chloride (36.6 mL, 0.52 mol) was added to a stirred suspension of 1-isopropyl-2-oxo-1,2-dihydroquinoline-3-carboxylic acid (80 g, 0.35 mol) in toluene (600 mL) at 85° C. and the reaction mixture then heated to 95° C. for 2 h. The reaction mixture was cooled to room temperature and then added over 25 min to a vigorously stirred biphasic solution of (1S,3R,5R)-3-amino-8-azabicyclo[3.2.1]octane-8-carboxylic acid tert-butyl ester (78.2 g, 0.35 mol) and sodium hydroxide (69.2 g, 1.73 mol) in toluene/water (1:1) (1 L) at ° C. After 1 h, the layers were allowed to separate and the organic phase concentrated under reduced pressure. The aqueous phase was washed with EtOAc (1 L) and then (500 mL) and the combined organic extracts used to dissolve the concentrated organic residue. This solution was washed with 1M H$_3$PO$_4$ (500 mL), sat. aq. NaHCO$_3$ (500 mL) and brine (500 mL), dried over MgSO$_4$, filtered and concentrated under reduced pressure to yield the title intermediate (127.9 g, approx. 84%) as a yellow solid. $^1$H NMR (CDCl$_3$): 1.47 (s, 9H), 1.67 (d, 6H), 1.78-1.84 (m, 2H), 2.04-2.18 (m, 6H), 4.20-4.39 (m, 3H), 5.65 (bs, 1H), 7.26 (dd. 1H), 7.63 (m, 2H), 7.75 (dd, 1H), 8.83 (s, 1H), 10.63 (d, 1H).

f. Preparation of 1-isopropyl-2-oxo-1,2-dihydroquinoline-3-carboxylic acid {(1S,3R,5R)-8-azabicyclo[3.2.1]oct-3-yl}amide TFA (300 mL) was added to a stirred solution of the product of the previous step (127.9 g) in CH$_2$Cl$_2$ (600 mL) at 0° C. The reaction mixture was warmed to room temperature and stirred for 1 h and then concentrated under reduced pressure. The oily brown residue was then poured into a vigorously stirred solution of ether (3 L) and a solid precipitate formed immediately. The suspension was stirred overnight and then the solid collected by filtration and washed with ether to yield the title intermediate as its trifluoroacetic acid salt (131.7 g, 86% over two steps) as a light yellow solid. $^1$H NMR (CDCl$_3$): 1.68 (d, 6H), 2.10 (d, 2H), 2.33-2.39 (m, 4H), 2.44-2.61 (m, 2H), 4.08 (bs, 2H), 4.41 (m, 1H), 5.57 (bs, 1H), 7.31 (m. 1H), 7.66 (m, 2H), 7.77 (d, 1H), 8.83 (s, 1H), 9.38 (bd, 2H), 10.78 (d, 1H).

g. Preparation of 3-hydroxy-3'-{[1-isopropyl-2-oxo-1,2-dihydroquinolin-3-yl)carbonyl]amino}spiro[azetidine-1,8'-(1S,3R,5R)-8-azabicyclo[3.2.1]octane (Intermediate (XV) with $R^1$=H, $R^2$=isopropyl, $R^3$=H)

2-Bromomethyloxirane (10.72 mL, 129.5 mmol) was added to a stirred solution of 1-isopropyl-2-oxo-1,2-dihydroquinoline-3-carboxylic acid {(1S,3R,5R)-8-azabicyclo[3.2.1]oct-3-yl}amide trifluoroacetic acid salt (14.65 g, 43.2 mmol) in ethanol (150 mL) at room temperature. The reaction mixture was stirred for 36 h, at which time a solid precipitate formed. The solid was collected by filtration and washed with ethanol (70 mL) to yield the title intermediate as the bromide salt (8.4 g). (m/z): [M+H]$^+$ calcd for C$_{23}$H$_{30}$N$_3$O$_3$ 396.23; found, 396.5. Retention time (anal. HPLC: 2-50% MeCN/H$_2$O over 5 min)=4.13 min.

h. Preparation of 1-isopropyl-2-oxo-1,2-dihydroquinoline-3-carboxylic acid (1S,3R,5R)-8-{2-hydroxy-3-[2-(2-hydroxyethoxy)ethylamino]propyl}-8-azabicyclo[3.2.1]oct-3-yl)-amide (Intermediate (III) with $R^1$=H, $R^2$=isopropyl, $R^3$=H, n=1, Y=2-hydroxyethoxy)

3-Hydroxy-3'-{[1-isopropyl-2-oxo-1,2-dihydroquinolin-3-yl)carbonyl]amino}-spiro[azetidine-1,8'-(1S,3R,5R)-8-azabicyclo[3.2.1]octane, the product of step (g), (115 mg, 0.24 mmol), was added to 1.0 mL ethanol, 2-(2-aminoethoxy) ethanol (50.46 mg, 0.48 mmol) and N,N-diisopropylethylamine (93.06 mg, 0.72 mmol). The resulting mixture heated to 80° C. overnight, then concentrated under reduced pressure to provide the title compound as an intermediate of formula (III) which was used without further isolation or purification.

i. Synthesis of 1-isopropyl-2-oxo-1,2-dihydroquinoline-3-carboxylic acid [(1S,3R,5R)-8-(2-hydroxy-3-{[2-(2-hydroxyethoxy)ethyl]methanesulfonylamino}propyl)-8-azabicyclo[3.2.1]oct-3-yl]amide The product of step (h) above was dissolved in dichloromethane (1.0 mL). N,N-diisopropylethylamine (62.04 mg, 0.48 mmol) was added to the mixture, and the mixture was then cooled to 0° C. To this cold mixture was slowly added methanesulfonylchloride (93.06 mg, 0.528 mmol). After stirring at 0° C. for one hour, the reaction was quenched with 0.5 mL 50% CH$_3$CO$_2$H in H$_2$O, concentrated, redissolved in 1.5 mL 50% CH$_3$CO$_2$H in H$_2$O, and purified by reversed phase preparative HPLC to yield the title compound as trifluoroacetic acid salt. (m/z): [M+H]$^+$ calcd for C$_{28}$H$_{42}$N$_4$O$_7$S 579.29; found 579.2.

Example 2

Synthesis of 1-Isopropyl-2-oxo-1,2-dihydroquinoline-3-carboxylic acid ((1S,3R,5R)-8-{3-[(2-ethylsulfanylethyl)methanesulfonylamino]-2-hydroxypropyl}-8-azabicyclo[3.2.1]oct-3-yl)amide

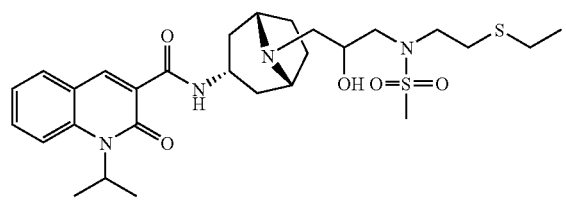

a. Preparation of 1-isopropyl-2-oxo-1,2-dihydroquinoline-3-carboxylic acid {(1S,3R,5R)-8-[3-(2-ethylsulfanylethylamino)-2-hydroxypropyl]-8-azabicyclo[3.2.1]oct-3-yl}-amide (Intermediate (III) with $R^1$=H, $R^2$=isopropyl, $R^3$=H, n=1, Y=—SCH$_2$CH$_3$)

Using the process and reagents described in Example 1, step (h) above, except substituting (ethylthio)ethylamine for 2-(2-aminoethoxy)ethanol, the title intermediate of formula (III) was prepared. After the reaction mixture was concentrated, the residue was diluted with 1.5 mL 50% CH$_3$CO$_2$H in H$_2$O and purified by reversed phase preparative HPLC.

b. Synthesis of 1-isopropyl-2-oxo-1,2-dihydroquinoline-3-carboxylic acid ((1S,3R,5R)-8-{3-[(2-ethylsulfanylethyl)methanesulfonylamino]-2-hydroxypropyl}-8-azabicyclo-[3.2.1]oct-3-yl)amide A dichloromethane solution of 1,8-diazabicyclo[5.4.0]undec-7-ene (DBU) (0.668 M, 67 µL was added to the product of the previous step (11.1 mg, 0.015 mmol). The mixture was cooled to 0° C. before a solution of methanesulfonylchloride in dichloromethane (1.268 M, 11.8 µL) was added. The reaction progress was monitored by mass spectrum for approximately one hour until the desired product was observed together with starting material. Another 11.8 µL (1.268M) dichloromethane solution of methanesulfonylchloride was added. The mixture was stirred at 0° C. for another hour. Then the reaction was quenched with a mixture of 50% CH$_3$COOH in water, concentrated, redissolved in 50% CH$_3$COOH in water, and purified by reversed phase preparative HPLC to yield the title compound as a trifluoroacetic acid salt. (m/z): [M+H]$^+$ calcd for C$_{28}$H$_{42}$N$_4$O$_5$S$_2$ 579.27; found 579.2.

Example 3

Synthesis of (2-Hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-[2-(4-methanesulfonylpiperazin-1-yl)ethyl]-carbamic acid methyl ester

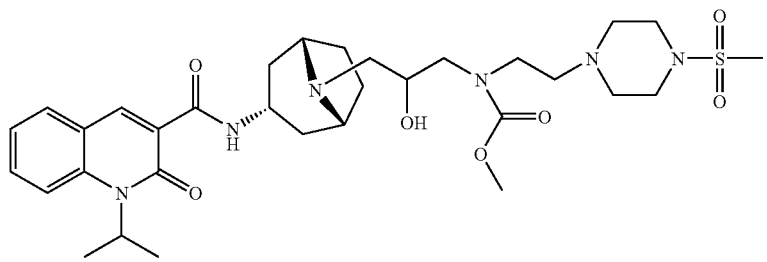

a. Preparation of 1-isopropyl-2-oxo-1,2-dihydroquinoline-3-carboxylic acid {8-[3-(2,2-dimethoxyethylamino)-2-hydroxy-propyl]-8-(1S,3R,5R)-azabicyclo[3.2.1]oct-3-yl}amide To a stirred solution of 3-hydroxy-3'-{[1-isopropyl-2-oxo-1,2-dihydroquinolin-3-yl)carbonyl]amino}spiro[azetidine-1,8'-(1S,3R,5R)-8-azabicyclo[3.2.1]octane, the product of step (g) of Example 1, (6.8 g, 14.27 mmol) in ethanol (150 mL) was added DIPEA (3.69 g, 28.55 mmol) and 2,2-dimethoxyethylamine (4.5 g, 42.82 mmol). The reaction was heated to reflux and stirred overnight. The reaction solution was allowed to cool to ambient temperature and was then concentrated under reduced pressure. The concentrate was diluted with DCM (500 mL) and then extracted with 1M $H_3PO_4$ (500 mL). The aqueous phase was washed with DCM (2×200 mL), basified to pH=12 (40% NaOH) and extracted with DCM (3×300 mL). The organic phase was dried (MgSO$_4$), filtered and concentrated under reduced pressure to yield the title intermediate (6.5 g) as a light brown, viscous oil. (m/z): [M+H]$^+$ calcd for $C_{27}H_{40}N_4O_5$ 501.30; found 501.6.

b. Preparation of (2,2-Dimethoxyethyl)-(2-hydroxy-3-{(1S,3R,5R)-3-[(1-isopropyl-2-oxo-1,2-dihydro-quinoline-3-carbonyl)amino]-8-azabicyclo[3.2.1]oct-8-yl}propyl)-carbamic acid methyl ester To a stirred solution of the product of the previous step (2.16 g, 4.315 mmol) in DCM (50 mL) was added DIPEA (0.585 g, 4.531 mmol). The reaction was cooled to 0° C. and methylchloroformate (0.428 g, 4.531 mmol) was added dropwise. The stirred reaction was allowed to warm to room temperature overnight. The reaction solution was concentrated under reduced pressure, dissolved in 50% aqueous acetonitrile (10 mL), and purified by preparative HPLC. The clean fractions were combined and lyophilized to yield the title intermediate (1.2 g) as a white solid. (m/z): [M+H]$^+$ calcd for $C_{29}H_{42}N_4O_7$ 559.31; found 559.6.

c. Preparation of (2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-(2-oxo-ethyl)-carbamic acid methyl ester (Intermediate (V) with R$^1$=H, R$^2$=isopropyl, R$^3$=H, and R$^4$ is —C(O)OCH$_3$)

To the product of the previous step (1.1 g, 1.635 mmol) was added 50% HCl (10 mL). The reaction solution was stirred for 30 minutes, and then excess HCl was evaporated under reduced pressure. The resulting solution was diluted with 50% aqueous acetonitrile and lyophilized, to yield the title intermediate (0.875 g) as a pale yellow solid. (m/z): [M+H]$^+$ calcd for $C_{27}H_{36}N_4O_6$ 513.26; found 513.4.

d. Synthesis of (2-hydroxy-3-{(1S,3R,5R)-3-[(1-isopropyl-2-oxo-1,2-dihydro-quinoline-3-carbonyl)amino]-8-azabicyclo[3.2.1]oct-8-yl}propyl)-[2-(4-methanesulfonyl-piperazin-1-yl)ethyl]-carbamic acid methyl ester To a solution of piperazinesulfonamide (25.5 mg, 0.0918 mmol) and DIPEA (71 mg, 0.55 mmol) in DCM (0.5 mL) was added a solution of the product of the previous step (0.017 g, 0.031 mmol) in DCM (0.5 mL), and the solution was agitated for 5 minutes. Sodium triacetoxyborohydride (0.0091 g, 0.043 mmol) was added and the resulting suspension was agitated for 1 hour. The solution was concentrated under reduced pressure to dryness, then dissolved in 50% aqueous acetonitrile and purified by HPLC. The purified fractions were combined and lyophilized to yield the title compound (0.03 g) as a trifluoroacetate salt. (m/z): [M+H]$^+$ calcd for $C_{32}H_{48}N_6O_7S$ 661.34; found, 661.2. Retention time (anal. HPLC: 5-60% MeCN/H$_2$O over 5 min)=2.11 min.

Example 4

Synthesis of 1-Isopropyl-2-oxo-1,2-dihydroquinoline-3-carboxylic acid {(1S,3R,5R)-8-[3-(acetyl-{2-[(2-methanesulfonylethyl)-methylamino]-ethyl}amino)-2-hydroxypropyl]-8-azabicyclo[3.2.1]oct-3-yl}amide

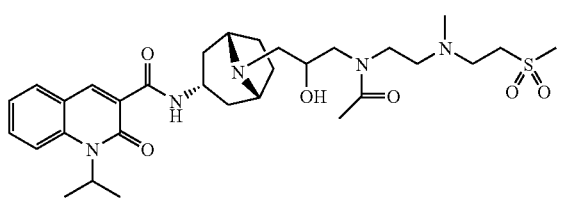

a. Preparation of 1-isopropyl-2-oxo-1,2-dihydroquinoline-3-carboxylic acid ((1S,3R,5R)-8-{3-[acetyl-(2,2-dimethoxyethyl)amino]-2-hydroxypropyl}-8-azabicyclo-[3.2.1]oct-3-yl)-amide Using the synthetic process and reagents described in Example 3, Step b, except substituting acetyl chloride (0.355 g, 4.531 mmol) for methylchloroformate, the title intermediate (1.2 g) was prepared as a white solid. (m/z): [M+H]+ calcd for $C_{29}H_{42}N_4O_6$ 543.31; found 543.8.

b. Preparation of 1-isopropyl-2-oxo-1,2-dihydroquinoline-3-carboxylic acid ((1S,3R,5R)-8-{3-[acetyl-(2-oxo-ethyl)-amino]-2-hydroxy-propyl}-8-aza-bicyclo[3.2.1]oct-3-yl)-amide (Intermediate (V) with $R^1$=H, $R^2$=isopropyl, $R^3$=H, and $R^4$ is —C(O)CH$_3$)

To the product of the previous step (1.0 g, 1.523 mmol) was added 50% HCl (10 mL). The reaction solution was stirred for 30 minutes, and then excess HCl was evaporated at reduced pressure. The resulting solution was diluted with 50% aqueous acetonitrile and lyophilized, to yield the title intermediate (0.991 g) as a pale yellow solid. (m/z): [M+H]+ calcd for $C_{27}H_{36}N_4O_5$ 497.27; found 497.6.

c. Synthesis of 1-isopropyl-2-oxo-1,2-dihydroquinoline-3-carboxylic acid {(1S,3R,5R)-8-[3-(acetyl-{2-[(2-methanesulfonylethyl)-methylamino]-ethyl}amino)-2-hydroxypropyl]-8-azabicyclo[3.2.1]oct-3-yl}amide To a solution of (2-methanesulfonylethyl)methylamine (13.7 mg, 0.103 mmol) and DIPEA (27.1 mg, 0.21 mmol) in DCM (0.5 mL) was added a solution of the product of the previous step (0.019 g, 0.035 mmol) in DCM (0.5 mL). The solution was agitated for 5 minutes. Sodium triacetoxyborohydride (0.010 g, 0.048 mmol) was added and the resulting suspension was agitated for 1 hour. The solution was concentrated under reduced pressure to dryness, then dissolved in 50% aqueous acetonitrile and purified by HPLC. The purified fractions were combined and lyophilized to yield the title compound (0.005 g) as a trifluoroacetate salt. (m/z): [M+H]+ calcd for $C_{31}H_{47}N_5O_6S$ 618.33; found, 618.2. Retention time (anal. HPLC: 5-60% MeCN/H$_2$O over 5 min)=2.01 min.

Using the methods described in Examples 1-4, and substituting the appropriate reagents, the following compounds listed in Tables 1-6 were prepared. In all of the compounds of the invention depicted in Tables 1-6, the quinolinone-carboxamide is endo to the azabicyclooctane group.

TABLE 1

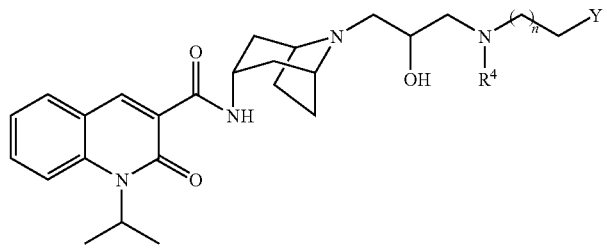

(II-a)

| # | n | R$^4$ | Y | Molecular Formula | Calc'd [M + H] | Obsd [M + H] |
|---|---|---|---|---|---|---|
| 1 | 1 | —SO$_2$CH$_3$ | —OCH$_2$CH$_2$OH | C$_{28}$H$_{42}$N$_4$O$_7$S | 575.29 | 575.2 |
| 2 | 1 | —SO$_2$CH$_3$ | —SCH$_2$CH$_3$ | C$_{28}$H$_{42}$N$_4$O$_5$S$_2$ | 579.27 | 579.2 |
| 3 | 0 | —SO$_2$CH$_3$ | (tetrahydrofuran-2-yl) | C$_{29}$H$_{42}$N$_4$O$_6$S | 575.29 | 575.2 |
| 4 | 2 | —SO$_2$CH$_3$ | (imidazol-1-yl) | C$_{30}$H$_{42}$N$_6$O$_5$S | 599.30 | 599.2 |

TABLE 1-continued (II-a)

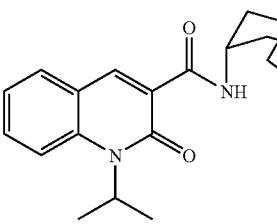

| # | n | R⁴ | Y | Molecular Formula | Calc'd [M + H] | Obsd [M + H] |
|---|---|---|---|---|---|---|
| 5 | 1 | —SO$_2$CH$_3$ | 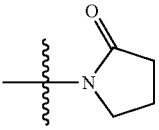 | C$_{34}$H$_{43}$N$_5$O$_5$S | 634.31 | 634.2 |
| 6 | 1 | —SO$_2$CH$_3$ | —NHSO$_2$CH$_3$ | C$_{27}$H$_{41}$N$_5$O$_7$S$_2$ | 612.25 | 612.2 |
| 7 | 2 | —SO$_2$CH$_3$ | 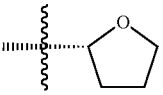 | C$_{31}$H$_{45}$N$_5$O$_6$S | 616.32 | 616.2 |
| 8 | 0 | —SO$_2$CH$_3$ | 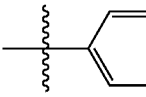 | C$_{29}$H$_{42}$N$_4$O$_6$S | 575.29 | 575.2 |
| 9 | 1 | —SO$_2$CH$_3$ | 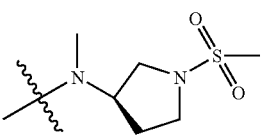 | C$_{31}$N$_{41}$N$_5$O$_5$S | 596.29 | 596.2 |
| 10 | 1 | —SO$_2$CH$_3$ | —OCH3 | C$_{27}$H$_{40}$N$_4$O$_6$S | 549.71 | 549.2 |
| 11 | 1 | —C(O)OCH$_3$ | 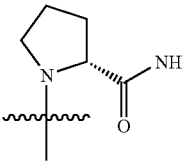 | C$_{33}$H$_{50}$N$_6$O$_7$S | 675.36 | 675.2 |
| 12 | 1 | —C(O)OCH$_3$ | 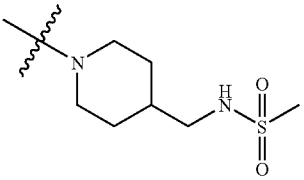 | C$_{32}$H$_{46}$N$_6$O$_6$ | 611.36 | 611.2 |
| 13 | 1 | —C(O)OCH$_3$ | —N(CH$_3$)SO$_2$N(CH$_3$)$_2$ | C$_{33}$H$_{53}$N$_7$O$_7$S | 692.38 | 692.2 |
| 14 | 1 | —C(O)OCH$_3$ | —N(CH$_2$CH$_2$OCH$_3$)—(CH$_2$)$_2$N(CH$_3$)SO$_2$CH$_3$ | C$_{34}$H$_{54}$N$_6$O$_8$S | 707.38 | 707.2 |
| 15 | 1 | —C(O)OCH$_3$ | —N(CH$_3$)CH$_2$—C(O)N(CH$_3$)$_2$ | C$_{32}$H$_{48}$N$_6$O6 | 613.37 | 613.2 |
| 16 | 1 | —C(O)OCH$_3$ | —N(CH$_3$)CH$_2$C(O)NH$_2$ | C$_{30}$H$_{44}$N$_6$O$_6$ | 585.34 | 585.2 |
| 17 | 1 | —C(O)CH$_3$ |  | C$_{34}$H$_{52}$N$_6$O$_6$S | 673.38 | 673.2 |
| 18 | 1 | —C(O)CH$_3$ | —N(CH$_3$)CH$_2$CH$_2$N(CH$_3$)SO$_2$CH$_3$ | C$_{32}$H$_{50}$N$_6$O$_6$S | 647.36 | 647.2 |
| 19 | 1 | —C(O)CH$_3$ | —N(CH$_3$)CH$_2$CH$_2$NHSO$_2$CH$_3$ | C$_{31}$H$_{48}$N$_6$O$_6$S | 633.35 | 633.2 |

TABLE 1-continued

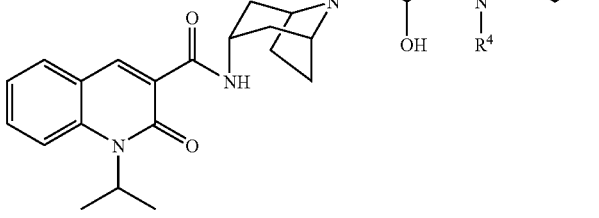

(II-a)

| # | n | R⁴ | Y | Molecular Formula | Calc'd [M + H] | Obsd [M + H] |
|---|---|---|---|---|---|---|
| 20 | 1 | —C(O)CH₃ | —N(CH₃)CH₂CH₂N(CH₃)C(O)OCH₃ | $C_{33}H_{50}N_6O_6$ | 627.39 | 627.2 |
| 21 | 1 | —C(O)CH₃ | —N(CH₃)CH₂CH₂N(CH₃)SO₂N(CH₃)₂ | $C_{33}H_{53}N_7O_6S$ | 676.39 | 676.2 |
| 22 | 1 | —C(O)CH₃ | —N(CH₃)CH₂CH₂SO₂CH₃ | $C_{31}H_{47}N_5O_6S$ | 618.33 | 618.2 |
| 23 | 1 | —C(O)CH₃ | —N(CH₂CH₂OCH₃)—(CH₂)₂SO₂CH₃ | $C_{33}H_{51}N_5O_7S$ | 662.36 | 662.2 |
| 24 | 1 | —C(O)CH₃ | —N(CH₂CH₂OCH₃)—(CH₂)₂N(CH₃)SO₂CH₃ | $C_{34}H_{54}N_6O_7S$ | 691.39 | 691.3 |
| 25 | 1 | —C(O)CH₃ | —N(CH₃)CH₂C(O)N(CH₃)₂ | $C_{32}H_{48}N_6O_5$ | 597.38 | 597.3 |
| 26 | 1 | —C(O)CH₃ | —N(CH₃)CH₂C(O)NH₂ | $C_{30}H_{44}N_6O_5$ | 569.35 | 569.2 |
| 27 | 1 | —C(O)CH₃ | 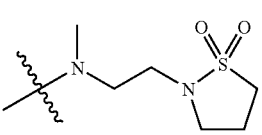 | $C_{33}H_{50}N_6O_6S$ | 659.36 | 659.2 |

TABLE 2

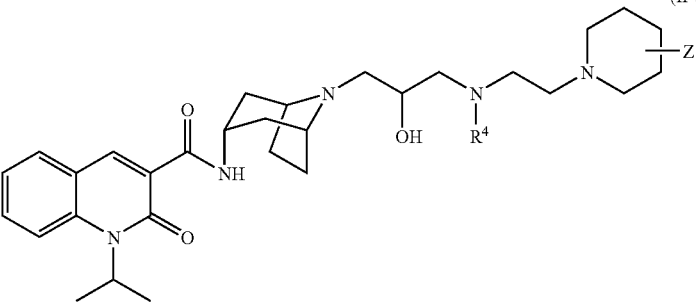

(II-b)

| # | R⁴ | Z | Molecular Formula | Calc'd [M + H] | Obsd [M + H] |
|---|---|---|---|---|---|
| 1 | —C(O)OCH₃ | 3-N(CH₃)SO₂CH₃ | $C_{34}H_{52}N_6O_7S$ | 689.37 | 689.2 |
| 2 | —C(O)OCH₃ | 3-N(CH₃)C(O)OCH₃ | $C_{35}H_{52}N_6O_7$ | 669.4 | 669.3 |
| 3 | —C(O)OCH₃ | 3-N(CH₃)C(O)CH₃ | $C_{35}H_{52}N_6O_6$ | 653.4 | 653.3 |
| 4 | —C(O)OCH₃ | 3-NHSO₂N(CH₃)₂ | $C_{34}H_{53}N_7O_7S$ | 704.38 | 704.2 |
| 5 | —C(O)OCH₃ | 3-NHC(O)OCH₃ | $C_{34}H_{50}N_6O_7$ | 655.38 | 655.2 |
| 6 | —C(O)OCH₃ | 3-NHC(O)CH₃ | $C_{34}H_{50}N_6O_6$ | 639.39 | 639.3 |
| 7 | —C(O)OCH₃ | 3-NHC(O)N(CH₃)₂ | $C_{35}H_{53}N_7O_6$ | 668.42 | 668.3 |
| 8 | —C(O)OCH₃ | 3-C(O)NH₂ | $C_{33}H_{48}N_6O_6$ | 625.37 | 625.2 |
| 9 | —C(O)OCH₃ | 4-OC(O)N(CH₃)₂ | $C_{35}H_{52}N_6O_7$ | 669.4 | 669.2 |
| 10 | —C(O)CH₃ | 3-N(CH₃)SO₂CH₃ | $C_{34}H_{52}N_6O_6S$ | 673.38 | 673.2 |
| 11 | —C(O)CH₃ | 3-N(CH₃)C(O)OCH₃ | $C_{35}H_{52}N_6O_6$ | 653.4 | 653.3 |
| 12 | —C(O)CH₃ | 3-N(CH₃)C(O)CH₃ | $C_{35}H_{52}N_6O_5$ | 637.41 | 637.3 |
| 13 | —C(O)CH₃ | 3-NHSO₂N(CH₃)₂ | $C_{34}H_{53}N_7O_6S$ | 688.39 | 688.2 |
| 14 | —C(O)CH₃ | 3-NHC(O)CH₃ | $C_{34}H_{50}N_6O_5$ | 623.39 | 623.3 |
| 15 | —C(O)CH₃ | 3-C(O)NH₂ | $C_{33}H_{48}N_6O_5$ | 609.38 | 609.2 |
| 16 | —C(O)CH₃ | 4-OC(O)N(CH₃)₂ | $C_{35}H_{52}N_6O_6$ | 653.4 | 653.3 |

TABLE 3

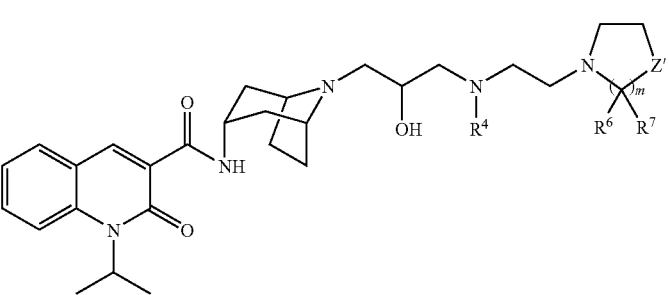

| # | R[4] | (CR[6]R[7])m | Z' | Molecular Formula | Calc'd [M + H] | Obsd [M + H] |
|---|---|---|---|---|---|---|
| 1 | —C(O)OCH$_3$ | —CH(CH$_2$OH)CH$_2$— | O | C$_{32}$H$_{47}$N$_5$O$_7$ | 614.36 | 614.3 |
| 2 | —C(O)OCH$_3$ | —(CH$_2$)$_2$— | NSO$_2$CH$_3$ | C$_{32}$H$_{48}$N$_6$O$_7$S | 661.34 | 661.2 |
| 3 | —C(O)OCH$_3$ | —(CH$_2$)$_2$— | NC(O)N(CH$_3$)$_2$ | C$_{34}$H$_{51}$N$_7$O$_6$ | 654.4 | 654.3 |
| 4 | —C(O)OCH$_3$ | —(CH$_2$)$_3$— | NC(O)CH$_3$ | C$_{34}$H$_{50}$N$_6$O$_6$ | 639.39 | 639.3 |
| 5 | —C(O)OCH$_3$ | —(CH$_2$)$_2$— | NC(O)NHCH$_3$ | C$_{33}$H$_{49}$N$_7$O$_6$ | 640.38 | 640.2 |
| 6 | —C(O)OCH$_3$ | —(CH$_2$)$_2$— | SO$_2$ | C$_{31}$H$_{45}$N$_5$O$_7$S | 632.31 | 632.3 |
| 7 | —C(O)OCH$_3$ | —(CH$_2$)$_2$— | NC(O)NH$_2$ | C$_{32}$H$_{47}$N$_7$O$_6$ | 626.37 | 626.2 |
| 8 | —C(O)CH$_3$ | —CH(CH$_2$OH)CH$_2$— | O | C$_{32}$H$_{47}$N$_5$O$_6$ | 598.36 | 598.2 |
| 9 | —C(O)CH$_3$ | —(CH$_2$)$_2$— | NC(O)N(CH$_3$)$_2$ | C$_{34}$H$_{51}$N$_7$O$_5$ | 638.41 | 638.2 |
| 10 | —C(O)CH$_3$ | —(CH$_2$)$_3$— | NSO$_2$CH$_3$ | C$_{33}$H$_{50}$N$_6$O$_6$S | 659.36 | 659.2 |
| 11 | —C(O)CH$_3$ | —(CH$_2$)$_3$— | NC(O)CH$_3$ | C$_{34}$H$_{50}$N$_6$O$_5$ | 623.39 | 623.3 |
| 12 | —C(O)CH$_3$ | —(CH$_2$)$_2$— | NC(O)NH$_2$ | C$_{32}$H$_{47}$N$_7$O$_5$ | 610.37 | 610.2 |
| 13 | —C(O)CH$_3$ | —(CH$_2$)$_2$— | SO$_2$ | C$_{31}$H$_{45}$N$_5$O$_6$S | 616.32 | 616.3 |

TABLE 4

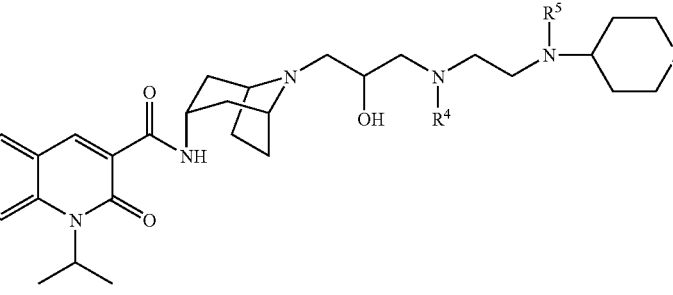

| # | R[4] | R[5] | Z' | Molecular Formula | Calc'd [M + H] | Obsd [M + H] |
|---|---|---|---|---|---|---|
| 1 | —C(O)OCH$_3$ | —CH$_3$ | SO$_2$ | C$_{33}$H$_{49}$N$_5$O$_7$S | 660.35 | 660.2 |
| 2 | —C(O)CH$_3$ | —CH$_3$ | SO$_2$ | C$_{33}$H$_{49}$N$_5$O$_6$S | 644.35 | 644.2 |

TABLE 5

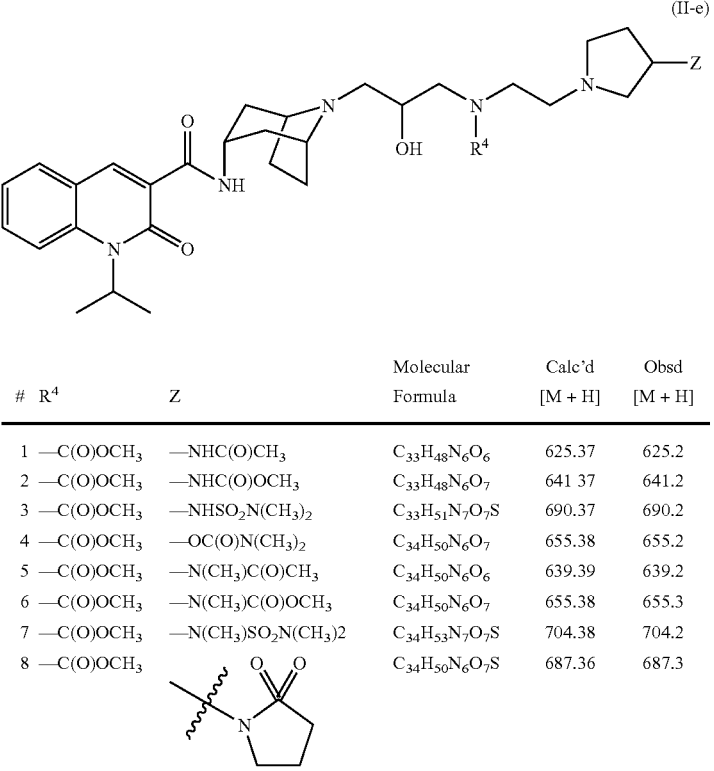

(II-e)

| # | R⁴ | Z | Molecular Formula | Calc'd [M + H] | Obsd [M + H] |
|---|---|---|---|---|---|
| 1 | —C(O)OCH$_3$ | —NHC(O)CH$_3$ | C$_{33}$H$_{48}$N$_6$O$_6$ | 625.37 | 625.2 |
| 2 | —C(O)OCH$_3$ | —NHC(O)OCH$_3$ | C$_{33}$H$_{48}$N$_6$O$_7$ | 641.37 | 641.2 |
| 3 | —C(O)OCH$_3$ | —NHSO$_2$N(CH$_3$)$_2$ | C$_{33}$H$_{51}$N$_7$O$_7$S | 690.37 | 690.2 |
| 4 | —C(O)OCH$_3$ | —OC(O)N(CH$_3$)$_2$ | C$_{34}$H$_{50}$N$_6$O$_7$ | 655.38 | 655.2 |
| 5 | —C(O)OCH$_3$ | —N(CH$_3$)C(O)CH$_3$ | C$_{34}$H$_{50}$N$_6$O$_6$ | 639.39 | 639.2 |
| 6 | —C(O)OCH$_3$ | —N(CH$_3$)C(O)OCH$_3$ | C$_{34}$H$_{50}$N$_6$O$_7$ | 655.38 | 655.3 |
| 7 | —C(O)OCH$_3$ | —N(CH$_3$)SO$_2$N(CH$_3$)2 | C$_{34}$H$_{53}$N$_7$O$_7$S | 704.38 | 704.2 |
| 8 | —C(O)OCH$_3$ | (pyrrolidinyl sulfonyl group) | C$_{34}$H$_{50}$N$_6$O$_7$S | 687.36 | 687.3 |
| 9 | —C(O)CH$_3$ | —NHC(O)CH$_3$ | C$_{33}$H$_{48}$N$_6$O$_5$ | 609.38 | 609.2 |
| 10 | —C(O)CH$_3$ | —NHC(O)OCH$_3$ | C$_{33}$H$_{48}$N$_6$O$_6$ | 625.37 | 625.2 |
| 11 | —C(O)CH$_3$ | —NHSO$_2$N(CH$_3$)$_2$ | C$_{33}$H$_{51}$N$_7$O$_6$S | 674.37 | 674.2 |
| 12 | —C(O)CH$_3$ | —OC(O)N(CH$_3$)$_2$ | C$_{34}$H$_{50}$N$_6$O$_6$ | 639.39 | 639.3 |
| 13 | —C(O)CH$_3$ | —N(CH$_3$)C(O)CH$_3$ | C$_{34}$H$_{50}$N$_6$O$_5$ | 623.39 | 623.3 |
| 14 | —C(O)CH$_3$ | —N(CH$_3$)C(O)OCH$_3$ | C$_{34}$H$_{50}$N$_6$O$_6$ | 639.39 | 639.2 |
| 15 | —C(O)CH$_3$ | —N(CH$_3$)SO$_2$N(CH$_3$)$_2$ | C$_{34}$H$_{53}$N$_7$O$_6$S | 688.39 | 688.2 |
| 16 | —C(O)CH$_3$ | —N(CH$_3$)C(O)N(CH$_3$)$_2$ | C$_{35}$H$_{53}$N$_7$O$_5$ | 652.42 | 652.3 |

TABLE 6

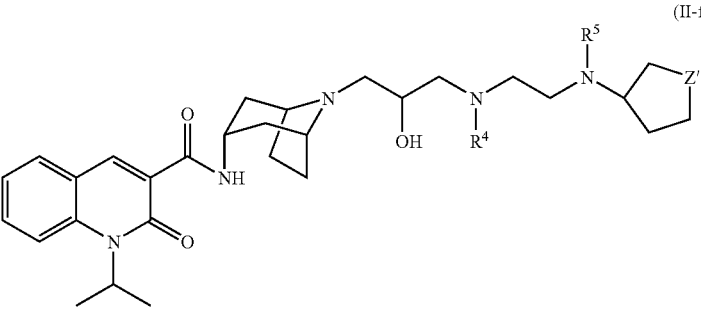

(II-f)

| # | R⁴ | R⁵ | Z' | Molecular Formula | Calc'd [M + H] | Obsd [M + H] |
|---|---|---|---|---|---|---|
| 1 | —C(O)OCH$_3$ | —CH$_3$ | NSO$_2$CH$_3$ | C$_{33}$H$_{50}$N$_6$O$_7$S | 675.36 | 675.2 |
| 2 | —C(O)OCH$_3$ | —CH$_3$ | NSO$_2$N(CH$_3$)$_2$ | C$_{34}$H$_{53}$N$_7$O$_7$S | 704.38 | 704.2 |
| 3 | —C(O)OCH$_3$ | —CH$_3$ | NC(O)OCH$_3$ | C$_{34}$H$_{50}$N$_6$O$_7$ | 655.38 | 655.3 |
| 4 | —C(O)CH$_3$ | —CH$_3$ | NSO$_2$N(CH$_3$)$_2$ | C$_{34}$H$_{53}$N$_7$O$_6$S | 688.39 | 688.3 |
| 5 | —C(O)CH$_3$ | —CH$_3$ | NC(O)OCH$_3$ | C$_{34}$H$_{50}$N$_6$O$_6$ | 639.39 | 639.3 |

Example 5

Radioligand Binding Assay on 5-HT$_{4(c)}$ Human Receptors a. Membrane Preparation 5-HT$_{4(c)}$ HEK-293 (human embryonic kidney) cells stably-transfected with human 5-HT$_{4(c)}$ receptor cDNA (Bmax=~6.0 pmol/mg protein, as determined using [$^3$H]-GR113808 membrane radioligand binding assay) were grown in T-225 flasks in Dulbecco's Modified Eagles Medium (DMEM) containing 4,500 mg/L D-glucose and pyridoxine hydrochloride (GIBCO-Invitrogen Corp., Carlsbad Calif.: Cat #11965) supplemented with 10% fetal bovine serum (FBS) (GIBCO-Invitrogen Corp.: Cat #10437), 2 mM L-glutamine and (100 units) penicillin-(100 μg) streptomycin/ml (GIBCO-Invitrogen Corp.: Cat #15140) in a 5% CO$_2$, humidified incubator at 37° C. Cells were grown under continuous selection pressure by the addition of 800 μg/mL geneticin (GIBCO-Invitrogen Corp.: Cat #10131) to the medium.

Cells were grown to roughly 60-80% confluency (<35 subculture passages). At 20-22 hours prior to harvesting, cells were washed twice and fed with serum-free DMEM. All steps of the membrane preparation were performed on ice. The cell monolayer was lifted by gentle mechanical agitation and trituration with a 25 mL pipette. Cells were collected by centrifugation at 1000 rpm (5 min).

For the membrane preparation, cell pellets were resuspended in ice-cold 50 mM 4-(2-hydroxyethyl)-1-piperazineethanesulphonic acid (HEPES), pH 7.4 (membrane preparation buffer) (40 mL/total cell yield from 30-40 T225 flasks) and homogenized using a polytron disrupter (setting 19, 2×10 s) on ice. The resultant homogenates were centrifuged at 1200 g for 5 min at 4° C. The pellet was discarded and the supernatant centrifuged at 40,000 g (20 min). The pellet was washed once by resuspension with membrane preparation buffer and centrifugation at 40,000 g (20 min). The final pellet was resuspended in 50 mM HEPES, pH 7.4 (assay buffer) (equivalent 1 T225 flask/1 mL). Protein concentration of the membrane suspension was determined by the method of Bradford (Bradford, 1976). Membranes were stored frozen in aliquots at −80° C.

b. Radioligand Binding Assays

Radioligand binding assays were performed in 1.1 mL 96-deep well polypropylene assay plates (Axygen) in a total assay volume of 400 μL containing 2 μg membrane protein in 50 mM HEPES pH 7.4, containing 0.025% bovine serum albumin (BSA). Saturation binding studies for determination of K$_d$ values of the radioligand were performed using [$^3$H]-GR113808 (Amersham Inc., Bucks, UK: Cat #TRK944; specific activity ~82 Ci/mmol) at 8-12 different concentrations ranging from 0.001 mM-5.0 nM. Displacement assays for determination of pK$_i$ values of compounds were performed with [$^3$H]-GR113808 at 0.15 nM and eleven different concentrations of compound ranging from 10 μM-100 μM.

Test compounds were received as 10 mM stock solutions in DMSO and diluted to 400 μM into 50 mM HEPES pH 7.4 at 25° C., containing 0.1% BSA, and serial dilutions (1:5) then made in the same buffer. Non-specific binding was determined in the presence of 1 μM unlabeled GR113808. Assays were incubated for 60 min at room temperature, and then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 μL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 1 μM GR113808. K$_i$ values for test compounds were calculated, in Prism, from the best-fit IC$_{50}$ values, and the K$_d$ value of the radioligand, using the Cheng-Prusoff equation (Cheng and Prusoff, *Biochemical Pharmacology*, 1973, 22, 3099-108): K$_i$=IC$_{50}$/(1+[L]/K$_d$) where [L]=concentration [$^3$H]-GR113808. Results are expressed as the negative decadic logarithm of the K$_i$ values, pK$_i$.

Test compounds having a higher pK$_i$ value in this assay have a higher binding affinity for the 5-HT$_4$ receptor. The compounds of the invention which were tested in this assay had a pK$_i$ value ranging from about 6.3 to about 8.5, typically ranging from about 7.0 to about 8.0.

Example 6

Radioligand Binding Assay on 5-HT$_{3A}$ Human Receptors: Determination of Receptor Subtype Selectivity a. Membrane Preparation 5-HT$_{3A}$ HEK-293 (human embryonic kidney) cells stably-transfected with human 5-HT$_{3A}$ receptor cDNA were obtained from Dr. Michael Bruess (University of Bonn, GDR) (Bmax=~9.0 pmol/mg protein, as determined using [$^3$H]-GR65630 membrane radioligand binding assay). Cells were grown in T-225 flasks or cell factories in 50% Dulbecco's Modified Eagles Medium (DMEM) (GIBCO-Invitrogen Corp., Carlsbad, Calif.: Cat #11965) and 50% Ham's F12 (GIBCO-Invitrogen Corp.: Cat #11765) supplemented with 10% heat inactivated fetal bovine serum (FBS) (Hyclone, Logan, Utah: Cat #SH30070.03) and (50 units) penicillin-(50 μg) streptomycin/ml (GIBCO-Invitrogen Corp.: Cat #15140) in a 5% CO$_2$, humidified incubator at 37° C.

Cells were grown to roughly 70-80% confluency (<35 subculture passages). All steps of the membrane preparation were performed on ice. To harvest the cells, the media was aspirated and cells were rinsed with Ca$^{2+}$, Mg$^{2+}$-free Dulbecco's phosphate buffered saline (dPBS). The cell monolayer was lifted by gentle mechanical agitation. Cells were collected by centrifugation at 1000 rpm (5 min). Subsequent steps of the membrane preparation followed the protocol described above for the membranes expressing 5-HT$_{4(c)}$ receptors.

b. Radioligand Binding Assays

Radioligand binding assays were performed in 96-well polypropylene assay plates in a total assay volume of 200 μL containing 1.5-2 μg membrane protein in 50 mM HEPES pH 7.4, containing 0.025% BSA assay buffer. Saturation binding studies for determination of K$_d$ values of the radioligand were performed using [$^3$H]-GR65630 (PerkinElmer Life Sciences Inc., Boston, Mass.: Cat #NET1101, specific activity ~85 Ci/mmol) at twelve different concentrations ranging from 0.005 nM to 20 nM. Displacement assays for determination of pK$_i$ values of compounds were performed with [$^3$H]-GR65630 at 0.50 nM and eleven different concentrations of compound ranging from 10 pM to 100 μM. Compounds were received as 10 mM stock solutions in DMSO (see section 3.1), diluted to 400 µM into 50 mM HEPES pH 7.4 at 25° C., containing 0.1% BSA, and serial (1:5) dilutions then made in the same buffer. Non-specific binding was determined in the presence of 10 µM unlabeled MDL72222. Assays were incubated for 60 min at room temperature, then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH7.4) to remove unbound radioactivity. Plates were dried, 35 µL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed using the non-linear regression procedure described above to determine $K_i$ values. The BOTTOM (curve minimum) was fixed to the value for non-specific binding, as determined in the presence of 10 µM MDL72222. The quantity [L] in the Cheng-Prusoff equation was defined as the concentration [$^3$H]-GR65630.

Selectivity for the 5-HT$_4$ receptor subtype with respect to the 5-HT$_3$ receptor subtype was calculated as the ratio $K_i$(5-HT$_{3A}$)/$K_i$(5-HT$_{4(c)}$). The compounds of the invention which were tested in this assay had a 5-HT$_4$/5-HT$_3$ receptor subtype selectivity ranging from about 50 to about 8000, typically ranging from about 100 to about 4000.

Example 7

Whole-Cell cAMP Accumulation Flashplate Assay with HEK-293 Cells Expressing Human 5-HT$_{4(c)}$ Receptors In this assay, the functional potency of a test compound was determined by measuring the amount of cyclic AMP produced when HEK-293 cells expressing 5-HT$_4$ receptors were contacted with different concentrations of test compound.

a. Cell Culture.

HEK-293 (human embryonic kidney) cells stably-transfected with cloned human 5-HT$_{4(c)}$ receptor cDNA were prepared expressing the receptor at two different densities: (1) at a density of about 0.5-0.6 pmol/mg protein, as determined using a [$^3$H]-GR113808 membrane radioligand binding assay, and (2) at a density of about 6.0 µmol/mg protein. The cells were grown in T-225 flasks in Dulbecco's Modified Eagles Medium (DMEM) containing 4,500 mg/L D-glucose (GIBCO-Invitrogen Corp.: Cat #11965) supplemented with 10% fetal bovine serum (FBS) (GIBCO-Invitrogen Corp.: Cat #10437) and (100 units) penicillin-(100 µg) streptomycin/ml (GIBCO-Invitrogen Corp.: Cat #15140) in a 5% $CO_2$, humidified incubator at 37° C. Cells were grown under continuous selection pressure by the addition of geneticin (800 µg/mL: GIBCO-Invitrogen Corp.: Cat #10131) to the medium.

b. Cell Preparation

Cells were grown to roughly 60-80% confluency. Twenty to twenty-two hours prior to assay, cells were washed twice, and fed, with serum-free DMEM containing 4,500 mg/L D-glucose (GIBCO-Invitrogen Corp.: Cat #11965). To harvest the cells, the media was aspirated and 10 mL Versene (GIBCO-Invitrogen Corp.: Cat #15040) was added to each T-225 flask. Cells were incubated for 5 min at RT and then dislodged from the flask by mechanical agitation. The cell suspension was transferred to a centrifuge tube containing an equal volume of pre-warmed (37° C.) dPBS and centrifuged for 5 min at 1000 rpm. The supernatant was discarded and the pellet was re-suspended in pre-warmed (37° C.) stimulation buffer (10 mL equivalent per 2-3 T-225 flasks). This time was noted and marked as time zero. The cells were counted with a Coulter counter (count above 8 µm, flask yield was 1-2×10$^7$ cells/flask). Cells were resuspended at a concentration of 5×10$^5$ cells/ml in pre-warmed (37° C.) stimulation buffer (as provided in the flashplate kit) and preincubated at 37° C. for 10 min.

cAMP assays were performed in a radioimmunoassay format using the Flashplate Adenylyl Cyclase Activation Assay System with $^{125}$I-cAMP (SMP004B, PerkinElmer Life Sciences Inc., Boston, Mass.), according to the manufacturer's instructions.

Cells were grown and prepared as described above. Final cell concentrations in the assay were 25×10$^3$ cells/well and the final assay volume was 100 µL. Test compounds were received as 10 mM stock solutions in DMSO, diluted to 400 µM into 50 mM HEPES pH 7.4 at 25° C., containing 0.1% BSA, and serial (1:5) dilutions then made in the same buffer. Cyclic AMP accumulation assays were performed with 11 different concentrations of compound ranging from 10 µM to 100 µM (final assay concentrations). A 5-HT concentration-response curve (10 µM to 100 µM) was included on every plate. The cells were incubated, with shaking, at 37° C. for 15 min and the reaction terminated by addition of 100 µl of ice-cold detection buffer (as provided in the flashplate kit) to each well. The plates were sealed and incubated at 4° C. overnight. Bound radioactivity was quantified by scintillation proximity spectroscopy using the Topcount (Packard Bio-Science Co., Meriden, Conn.).

The amount of cAMP produced per mL of reaction was extrapolated from the cAMP standard curve, according to the instructions provided in the manufacturer's user manual. Data were analyzed by nonlinear regression analysis with the GraphPad Prism Software package using the 3-parameter sigmoidal dose-response model (slope constrained to unity). Potency data are reported as pEC$_{50}$ values, the negative decadic logarithm of the EC$_{50}$ value, where EC$_{50}$ is the effective concentration for a 50% maximal response.

Test compounds exhibiting a higher pEC$_{50}$ value in this assay have a higher potency for agonizing the 5-HT$_4$ receptor. The compounds of the invention which were tested in this assay, for example, in the cell line (1) having a density of about 0.5-0.6 pmol/mg protein, had a pEC$_{50}$ value ranging from about 7.0 to about 9.0, typically ranging from about 7.5 to about 8.5.

Example 8

In Vitro Voltage Clamp Assay of Inhibition of Potassium Ion Current in Whole Cells Expressing the hERG Cardiac Potassium Channel CHO-K1 cells stably transfected with hERG cDNA were obtained from Gail Robertson at the University of Wisconsin. Cells were held in cryogenic storage until needed. Cells were expanded and passaged in Dulbecco's Modified Eagles Medium/F12 supplemented with 10% fetal bovine serum and 200 µg/1 mL geneticin. Cells were seeded onto poly-D-lysine (100 µg/mL) coated glass coverslips, in 35 mm$^2$ dishes (containing 2 mL medium) at a density that enabled isolated cells to be selected for whole cell voltage-clamp studies. The dishes were maintained in a humidified, 5% $CO_2$ environment at 37° C.

Extracellular solution was prepared at least every 7 days and stored at 4° C. when not in use. The extracellular solution contained (mM): NaCl (137), KCl (4), CaCl$_2$ (1.8), MgCl$_2$ (1), Glucose (10), 4-(2-hydroxyethyl)-1-piperazineethanesulphonic acid (HEPES) (10), pH 7.4 with NaOH. The extracellular solution, in the absence or presence of test compound, was contained in reservoirs, from which it flowed into the recording chamber at approximately 0.5 mL/min. The intracellular solution was prepared, aliquoted and stored at −20° C. until the day of use. The intracellular solution contained (mM): KCl (130), MgCl$_2$ (1), ethylene glycol-bis(beta-aminoethyl ether) N,N,N',N'-tetra acetic acid salt (EGTA) (5), MGATP (5), 4-(2-hydroxyethyl)-1-piperazineethanesulphonic acid (HEPES) (10), pH 7.2 with KOH. All experiments were performed at room temperature (20-22° C.).

The coverslips on which the cells were seeded were transferred to a recording chamber and perfused continuously. Gigaohm seals were formed between the cell and the patch electrode. Once a stable patch was achieved, recording commenced in the voltage clamp mode, with the initial holding potential at −80 mV. After a stable whole-cell current was achieved, the cells were exposed to test compound. The standard voltage protocol was: step from the holding potential of −80 mV to +20 mV for 4.8 sec, repolarize to −50 mV for 5 see and then return to the original holding potential (−80 mV). This voltage protocol was run once every 15 sec (0.067 Hz). Peak current amplitudes during the repolarization phase were determined using pClamp software. Test compounds at a concentration of 3 μM were perfused over the cells for 5 minutes, followed by a 5-minute washout period in the absence of compound. Finally a positive control (cisapride, 20 nM) was added to the perfusate to test the function of the cell. The step from −80 mV to +20 mV activates the hERG channel, resulting in an outward current. The step back to −50 mV results in an outward tail current, as the channel recovers from inactivation and deactivates.

Peak current amplitudes during the repolarization phase were determined using pCLAMP software. The control and test article data were exported to Origin® (OriginLab Corp., Northampton Mass.) where the individual current amplitudes were normalized to the initial current amplitude in the absence of compound. The normalized current means and standard errors for each condition were calculated and plotted versus the time course of the experiment.

Comparisons were made between the observed K$^+$ current inhibitions after the five-minute exposure to either the test article or vehicle control (usually 0.3% DMSO). Statistical comparisons between experimental groups were performed using a two-population, independent t-test (Microcal Origin v. 6.0). Differences were considered significant at p<0.05.

The smaller the percentage inhibition of the potassium ion current in this assay, the smaller the potential for test compounds to change the pattern of cardiac repolarization when used as therapeutic agents. The compounds of the invention which were tested in this assay at a concentration of 3 μM exhibited an inhibition of the potassium ion current of less than about 20%, typically, less than about 15%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A pharmaceutical composition comprising a pharmaceutically-acceptable carrier and a compound of formula (I):

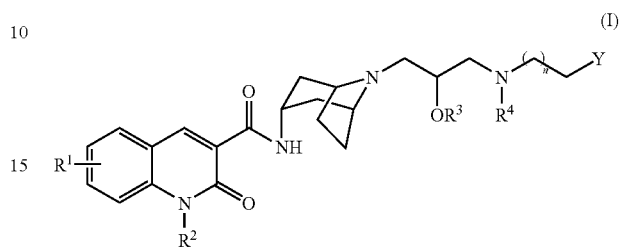

or a pharmaceutically-acceptable salt or stereoisomer thereof, wherein:

$R^1$ is hydrogen, halo, hydroxy, $C_{1-4}$alkyl, or $C_{1-4}$alkoxy;

$R^2$ is $C_{3-4}$alkyl or $C_{3-6}$cycloalkyl;

$R^3$ is hydrogen or $C_{1-3}$alkyl;

$R^4$ is —S(O)$_2$—C$_{1-3}$alkyl, —C(O)O—C$_{1-3}$alkyl or —C(O)—C$_{1-3}$alkyl;

n is an integer of 1, 2, or 3;

Y is selected from:

(a) a moiety of formula (a)

wherein:

Z is selected from —N(R$^8$)SO$_2$R$^a$, —N(R$^8$)C(O)R$^c$, —S(O$_2$)R$^8$, —N(R$^8$)C(O)OR$^d$, —N(R$^8$)C(O)NR$^e$R$^f$, —N(R$^8$)SO$_2$NR$^g$R$^h$, —C(O)NR$^i$R$^j$, —OC(O)NR$^k$R$^l$, —C(O)OR$^m$, —OR$^8$, —SR$^n$, cyano, hydroxy-substituted C$_{1-4}$alkyl, hydroxy-substituted C$_{1-3}$alkoxy, —CF$_3$, pyridinyl, thiomorpholinyl, thiazolidinyl, imidazolyl, indolyl, tetrahydrofuranyl, pyrrolidinyl and piperidinyl, wherein pyrrolidinyl is optionally substituted with oxo and piperidinyl is optionally substituted with 1 to 3 halo;

R$^5$ is selected from hydrogen and C$_{1-4}$alkyl, wherein C$_{1-4}$alkyl is optionally substituted with 1 to 2 substituents selected from hydroxy, halo, and C$_{1-3}$alkoxy;

m is an integer of 0, 1, 2, 3, 4, or 5;

R$^6$ and R$^7$ are independently selected from hydrogen, hydroxy, halo and C$_{1-4}$alkyl, wherein C$_{1-4}$alkyl is optionally substituted with 1 to 2 substituents selected from hydroxy, C$_{1-3}$alkoxy, and cyano;

R$^8$ is independently hydrogen or C$_{1-4}$alkyl, wherein C$_{1-4}$alkyl is optionally substituted with 1 to 2 substituents selected from hydroxy, C$_{1-3}$alkoxy, and cyano;

R$^a$ is hydrogen or C$_{1-4}$alkyl, wherein C$_{1-4}$alkyl is optionally substituted with —SO$_2$R$^b$, C$_{3-6}$cycloalkyl or with from 1 to 3 halo;

R$^c$ is hydrogen or C$_{1-4}$alkyl, wherein C$_{1-4}$alkyl is optionally substituted with 1 to 2 substituents selected from hydroxy and C$_{3-6}$cycloalkyl, or with from 1 to 3 halo;

and $R^b$, $R^d$, $R^e$, $R^f$, $R^g$, $R^h$, $R^i$, $R^j$, $R^k$, $R^l$, $R^m$, and $R^n$, are independently hydrogen or $C_{1-4}$alkyl;

or $R^5$ and $R^6$, $R^5$ and $R^8$, or $R^6$ and $R^8$, taken together form a $C_{2-5}$alkylene, wherein the $C_{2-5}$alkylene is optionally substituted with 1 to 2 substituents selected from hydroxy, halo and $C_{1-4}$alkyl, wherein $C_{1-4}$ alkyl is optionally substituted with 1 to 2 substituents selected from hydroxy, $C_{1-3}$alkoxy, and cyano;

or $R^8$ and $R^a$ taken together form a $C_{2-5}$alkylene;

provided that when m is 1, Z forms a carbon-carbon bond with the carbon atom bearing the substituents $R^6$ and $R^7$; and when m is 0, Z is selected from —$S(O_2)R^8$, —$C(O)NR^iR^j$, —$C(O)OR^m$, and —$CF_3$; and (c) —$SR^{10}$, wherein $R^{10}$ is hydrogen or $C_{1-4}$alkyl.

2. The pharmaceutical composition of claim 1 wherein Y is selected from:

(a) a moiety of formula (a), wherein Z is selected from —$N(R^8)SO_2R^a$, —$N(R^8)C(O)R^c$, —$S(O_2)R^8$, —$N(R^8)C(O)NR^eR^f$, —$C(O)NR^iR^j$, —$OC(O)NR^kR^l$, —$OR^8$, and cyano; and (c) —S—$C_{1-4}$alkyl.

3. The pharmaceutical composition of claim 1 wherein Y is a moiety of formula (a).

4. The pharmaceutical composition of claim 1 wherein the compound of formula (I) is a compound of formula (II):

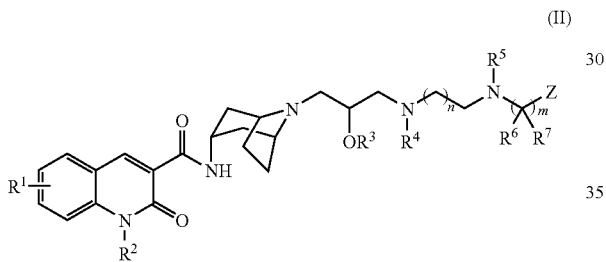

(II)

or a pharmaceutically-acceptable salt or stereoisomer thereof, wherein:

$R^1$ is hydrogen, halo, or $C_{1-3}$alkyl;

$R^2$ is $C_{3-4}$alkyl;

$R^3$ is hydrogen or methyl, $R^4$ is —$S(O)_2$—$C_{1-3}$alkyl, —$C(O)O$—$C_{1-3}$alkyl, or —$C(O)$—$C_{1-3}$alkyl;

n is an integer of 1 or 2;

$R^5$ is selected from hydrogen and $C_{1-4}$alkyl, wherein $C_{1-4}$alkyl is optionally substituted with 1 to 2 substituents selected from hydroxy, halo, and $C_{1-3}$alkoxy;

m is an integer of 1, 2, 3, 4, or 5;

$R^6$ and $R^7$ are independently selected from hydrogen and $C_{1-4}$alkyl, wherein $C_{1-4}$alkyl is optionally substituted with 1 to 2 substituents selected from hydroxy, $C_{1-3}$alkoxy, and cyano;

Z is selected from —$N(R^8)SO_2R^a$, —$N(R^8)C(O)R^c$, —$S(O_2)R^8$, —$N(R^8)C(O)OR^d$, —$N(R^8)C(O)NR^eR^f$, —$N(R^8)SO_2NR^gR^h$, —$C(O)NR^iR^j$, —$OC(O)NR^kR^l$, —$C(O)OR^m$, —$OR^8$, —$SR^n$, and cyano;

$R^8$ is independently hydrogen or $C_{1-4}$alkyl, wherein $C_{1-4}$alkyl is optionally substituted with 1 to 2 substituents selected from hydroxy, $C_{1-3}$alkoxy, and cyano;

$R^a$ is hydrogen or $C_{1-4}$alkyl, wherein $C_{1-4}$alkyl is optionally substituted with —$SO_2R^b$, $C_{3-6}$cycloalkyl or with from 1 to 3 halo;

$R^c$ is hydrogen or $C_{1-4}$alkyl, wherein $C_{1-4}$alkyl is optionally substituted with 1 to 2 substituents selected from hydroxy and $C_{3-6}$cycloalkyl, or with from 1 to 3 halo;

and $R^b$, $R^d$, $R^e$, $R^f$, $R^g$, $R^h$, $R^i$, $R^j$, $R^k$, $R^l$, $R^m$, and $R^n$, are independently hydrogen or $C_{1-4}$alkyl;

or $R^5$ and $R^6$, $R^5$ and $R^8$, or $R^6$ and $R^8$, taken together form a $C_{2-5}$alkylene, wherein the $C_{2-5}$alkylene is optionally substituted with 1 to 2 substituents selected from hydroxy, halo and $C_{1-4}$alkyl, wherein $C_{1-4}$alkyl is optionally substituted with 1 to 2 substituents selected from hydroxy, $C_{1-3}$alkoxy, and cyano;

or $R^8$ and $R^a$ taken together form a $C_{2-5}$alkylene.

5. The pharmaceutical composition of claim 4 wherein $R^1$ is hydrogen, $R^2$ is $C_{3-4}$alkyl, and $R^3$ is hydrogen.

6. The pharmaceutical composition of claim 5 wherein $R^4$ is selected from —$S(O)_2CH_3$, —$C(O)OCH_3$, and —$C(O)CH_3$.

7. The pharmaceutical composition of claim 6 wherein n is 1, and m is 1, 2 or 3.

8. The pharmaceutical composition of claim 7 wherein Z is selected from —$N(R^8)SO_2R^a$, —$N(R^8)C(O)R^c$, —$S(O_2)R^8$, and —$N(R^8)C(O)NR^eR^f$.

9. The pharmaceutical composition of claim 1 wherein the compound of formula (I) is selected from:

1-isopropyl-2-oxo-1,2-dihydroquinoline-3-carboxylic acid ((1S,3R,5R)-8-{3-[(2-ethylsulfanylethyl)methanesulfonylamino]-2-hydroxypropyl}-8-aza-bicyclo[3.2.1]oct-3-yl)amide;

(2-hydroxy-3-{(1S,3R,5R)-3-[(1-isopropyl-2-oxo-1,2-dihydro-quinoline-3-carbonyl)amino]-8-azabicyclo[3.2.1]oct-8-yl}propyl)-{2-[3-(methanesulfonylmethylamino)piperidin-1-yl]ethyl}-carbamic acid methyl ester;

[2-(3-acetylaminopiperidin-1-yl)ethyl]-(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-carbamic acid methyl ester;

[2-(3-acetylaminopyrrolidin-1-yl)ethyl]-(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-carbamic acid methyl ester;

(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-[2-(3-dimethylaminosulfonylaminopyrrolidin-1-yl)-ethyl]-carbamic acid methyl ester;

(2-hydroxy-3-{(1S,3R,5R)-3-[(1-isopropyl-2-oxo-1,2-dihydroquinoline-3-carbonyl)-amino]-8-azabicyclo[3.2.1]oct-8-yl}propyl)-[2-(3-dimethylaminosulfonylmethylaminopyrrolidin-1-yl)-ethyl]-carbamic acid methyl ester;

{2-[3-(1,1-dioxo-1λ⁶-isothiazolidin-2-yl)pyrrolidin-1-yl]ethyl}-(2-hydroxy-3-{(1S,3R,5R)-3-[(1-isopropyl-2-oxo-1,2-dihydroquinoline-3-carbonyl)amino]-8-azabicyclo[3.2.1]oct-8-yl}propyl)-carbamic acid methyl ester;

1-isopropyl-2-oxo-1,2-dihydroquinoline-3-carboxylic acid [(1S,3R,5R)-8-(3-{acetyl-[2-(3-carbamoylpiperidin-1-yl)ethyl]amino}-2-hydroxypropyl)-8-azabicyclo[3.2.1]oct-3-yl]-amide;

1-isopropyl-2-oxo-1,2-dihydroquinoline-3-carboxylic acid {(1S,3R,5R)-8-[3-(acetyl-{2-[4-(methanesulfonylaminomethyl)piperidin-1-yl]ethyl}amino)-2-hydroxypropyl]-8-aza-bicyclo[3.2.1]oct-3-yl}amide;

(1-{2-[acetyl-(2-hydroxy-3-{(1S,3R,5R)-3-[(1-isopropyl-2-oxo-1,2-dihydroquinoline-3-carbonyl)amino]-8- azabicyclo[3.2.1]oct-8-yl}propyl)amino]-ethyl}pyrrolidin-3-yl)-carbamic acid methyl ester;

1-isopropyl-2-oxo-1,2-dihydroquinoline-3-carboxylic acid {(1S,3R,5R)-8-[3-(acetyl-{2-[3-(dimethylaminosulfonylmethylamino)pyrrolidin-1-yl]ethyl}amino)-2-hydroxypropyl]-8-aza-bicyclo[3.2.1]oct-3-yl}amide;

1-isopropyl-2-oxo-1,2-dihydroquinoline-3-carboxylic acid {(1S,3R,5R)-8-[3-(acetyl-{2-[3-(trimethylureido)pyrrolidin-1-yl]ethyl}amino)-2-hydroxy-propyl]-8-azabicyclo-[3.2.1]oct-3-yl}amide;

1-isopropyl-2-oxo-1,2-dihydroquinoline-3-carboxylic acid {(1S,3R,5R)-8-[3-(acetyl-{2-[(1-dimethylsulfamoylpyrrolidin-3-yl)methylamino]ethyl}amino)-2-hydroxypropyl]-8-azabicyclo[3.2.1]oct-3-yl}amide;

1-isopropyl-2-oxo-1,2-dihydroquinoline-3-carboxylic acid ((1S,3R,5R)-8-{3[acetyl-(2-{[2-(methanesulfonylmethylamino)ethyl]methylamino}-ethyl)amino]-2-hydroxypropyl}-8-azabicyclo[3.2.1]oct-3-yl)amide;

1-isopropyl-2-oxo-1,2-dihydroquinoline-3-carboxylic acid {(1S,3R,5R)-8-[3-(acetyl-{2-[(2-methanesulfonylaminoethyl)methylamino]ethyl}amino)-2-hydroxypropyl]-8-aza-bicyclo[3.2.1]oct-3-yl}amide; and 1-isopropyl-2-oxo-1,2-dihydroquinoline-3-carboxylic acid ((1S,3R,5R)-8-{3-[acetyl-(2-{[2-(1,1-dioxo-1$\lambda^6$-isothiazolidin-2-yl)ethyl]methylamino}ethyl)amino]-2-hydroxypropyl}-8-azabicyclo[3.2.1]oct-3-yl)amide;

and pharmaceutically-acceptable salts and stereoisomers thereof.

10. A method of treating a mammal having a disease or medical condition mediated by treatment with a 5-HT$_4$ receptor agonist, wherein the disease or medical condition is chronic constipation, constipation-predominant irritable bowel syndrome, functional dyspepsia, gastroparesis, gastroesophageal reflux disease, or drug-induced delayed transit, the method comprising administering to the mammal, the pharmaceutical composition of claim 1.

11. The method of claim 10 wherein the disease or medical condition is chronic constipation or constipation-predominant irritable bowel syndrome.

12. The method of claim 10 wherein the disease or medical condition is functional dyspepsia, gastroparesis, gastroesophageal reflux disease, or drug-induced delayed transit.

13. A method of treating a disorder of reduced motility of the gastrointestinal tract in a mammal, the method comprising administering to the mammal, the pharmaceutical composition of claim 1.

14. A method of treating a mammal having a disease or medical condition mediated by treatment with a 5-HT$_4$ receptor agonist, wherein the disease or medical condition is chronic constipation, constipation-predominant irritable bowel syndrome, functional dyspepsia, gastroparesis, gastroesophageal reflux disease, or drug-induced delayed transit, the method comprising administering to the mammal, the pharmaceutical composition of claim 4.

15. The method of claim 14 wherein the disease or medical condition is chronic constipation or constipation-predominant irritable bowel syndrome.

16. The method of claim 14 wherein the disease or medical condition is functional dyspepsia, gastroparesis, gastroesophageal reflux disease, or drug-induced delayed transit.

* * * * *